US012614608B2

(12) United States Patent
Teramoto et al.

(10) Patent No.: US 12,614,608 B2
(45) Date of Patent: Apr. 28, 2026

(54) METHOD AND APPARATUS FOR CONSTRUCTING MICROBIAL IDENTIFICATION DATABASE

(71) Applicants: SHIMADZU CORPORATION, Kyoto (JP); NATIONAL INSTITUTE OF ADVANCED INDUSTRIAL SCIENCE AND TECHNOLOGY, Tokyo (JP)

(72) Inventors: Kanae Teramoto, Kyoto (JP); Koretsugu Ogata, Kyoto (JP); Yuji Sekiguchi, Tsukuba (JP); Daisuke Miura, Tsukuba (JP)

(73) Assignees: SHIMADZU CORPORATION, Kyoto (JP); NATIONAL INSTITUTE OF ADVANCED INDUSTRIAL, Tokyo (JP)

( * ) Notice: Subject to any disclaimer, the term of this patent is extended or adjusted under 35 U.S.C. 154(b) by 0 days.

(21) Appl. No.: 18/858,260

(22) PCT Filed: Apr. 3, 2023

(86) PCT No.: PCT/JP2023/013810
§ 371 (c)(1),
(2) Date: Jan. 2, 2025

(87) PCT Pub. No.: WO2023/204008
PCT Pub. Date: Oct. 26, 2023

(65) Prior Publication Data
US 2025/0273292 A1     Aug. 28, 2025

(30) Foreign Application Priority Data
Apr. 21, 2022     (JP) ................................. 2022-070280

(51) Int. Cl.
G16B 20/00     (2019.01)
G16B 35/00     (2019.01)

(52) U.S. Cl.
CPC ............. G16B 20/00 (2019.02); G16B 35/00 (2019.02)

(58) Field of Classification Search
CPC ................................. G16B 20/00; G16B 35/00
See application file for complete search history.

(56) References Cited

U.S. PATENT DOCUMENTS 7,020,559 B1 * 3/2006 Demirev ................... C12Q 1/04
                                                  702/19
2002/0138210 A1 * 9/2002 Wilkes ............... G01N 33/6851
                                                  702/28

(Continued)

FOREIGN PATENT DOCUMENTS

JP        2020182445 A     11/2020
JP        2021516970 A      7/2021

(Continued)

OTHER PUBLICATIONS

Sekiguchi et al., "A large-scale genomically predicted protein mass database enables rapid and broad-spectrum identification of bacterial and archaeal isolates by mass spectrometry", pp. 1-20 (Year: 2023).*

(Continued)

*Primary Examiner* — Jared M Bibbee
(74) *Attorney, Agent, or Firm* — Muir Patent Law, PLLC

(57)          ABSTRACT

A method of constructing a microbial identification database, the method comprising: (ST02) acquiring genome data for microorganisms from a genome database; (ST06) determining whether a criterion is satisfied by the genome data thus acquired; (ST16) for respective sets of the genome data that were determined that they satisfied the criterion, predicting proteins to be expressed; and (ST20A, 20C) con- (Continued)

structing a mass-to-charge ratio database including mass-to-charge ratio lists, the mass-to-charge ratio lists being predicted for the respective sets of the genome data based on the proteins thus predicted.

17 Claims, 10 Drawing Sheets

(56)                    References Cited

U.S. PATENT DOCUMENTS

| | | | |
|---|---|---|---|
| 2007/0178541 A1* | 8/2007 | Pedersen | G01N 33/6854 |
| | | | 435/5 |
| 2010/0057372 A1 | 3/2010 | Fagerquist et al. | |
| 2017/0004256 A1* | 1/2017 | Miyashita | G16B 30/00 |
| 2019/0056407 A1 | 2/2019 | Tamura et al. | |
| 2020/0063126 A1 | 2/2020 | Cheng et al. | |
| 2022/0270710 A1 | 8/2022 | Arikawa et al. | |

FOREIGN PATENT DOCUMENTS

| | | | |
|---|---|---|---|
| JP | 2021-193963 A | 12/2021 | |
| WO | 2017168743 A1 | 10/2017 | |
| WO | 2020/218555 A1 | 10/2020 | |

OTHER PUBLICATIONS

Hiroto Tamura et al., "Rapid Bacterial Discrimination by MALDI-TOF MS Based on Ribosomal Proteins as Biomarkers—Rapid Bacterial Discrimination by S10—Germs Method-", Reprinted from Shimadzu Review, vol. 70, No. 3•4, 2013 pp. 157-170.

PCT Written Opinion of International Searching Authority dated Jun. 13, 2023 for international application No. PCT/JP2023/013810.

Notice of Reasons for Refusal dated Nov. 11, 2025, for corresponding Japanese Patent Application No. 2024-516170.

Demirev et al., "Microorganism identification by mass spectrometry and protein database searches," Analytical chemistry 71.14 (1999): 2732-2738.

EESR dated Feb. 24, 2026, for corresponding application No. EP 23 79 1659.

Fagerquist et al., "Rapid identification of protein biomarkers of Escherichia coli O157: H7 by matrix-assisted laser desorption ionization-time-of-flight mass spectrometry and top-down proteomics," Analytical chemistry 82.7 (2010): 2717-2725.

Tamura et al., "Novel accurate bacterial discrimination by MALDI-time-of-flight MS based on ribosomal proteins coding in S10-spc-alpha operon at strain level S10-GERMS," Journal of the American Society for Mass Spectrometry 24.8 (2013): 1185-1193.

* cited by examiner

METHOD AND APPARATUS FOR CONSTRUCTING MICROBIAL IDENTIFICATION DATABASE

TECHNICAL FIELD

The present invention relates to a method and an apparatus for constructing a microbial identification database.

BACKGROUND ART

NPL 1 discloses that there are two potential approaches to identify microorganisms by mass spectrometry.

A first approach is a fingerprinting method, which is to identify unknown microorganisms by comparing measured mass spectra of the unknown microorganisms with a database of measured mass spectra of known microorganisms. However, this method has shortcomings; for example, the mass spectrum pattern of microorganisms tends to be affected greatly by the conditions of the medium and by the method for reproducing measurement.

With such shortcomings of a fingerprinting method as a backdrop, a second approach has been receiving attention, which is a bioinformatics-based method that uses a genome database. This method identifies unknown microorganisms by comparing measured mass spectra of the unknown microorganisms with a database of mass-to-charge ratios for proteins predicted from a genome database. The predicted mass-to-charge ratios are not affected by the conditions of the medium or the method for reproducing measurement, so this method can overcome the above-mentioned shortcoming of a fingerprinting method.

CITATION LIST

Non Patent Literature

NPL 1: Hiroto Tamura, et al., "Identification of Bacteria Using Ribosomal Protein as Biomarkers by MALDI-TOF MS—Rapid Identification of Bacteria by S10-GERMS method—", Shimadzu Review (offprint), vol. 70, the 3rd and 4th issues, 2013

SUMMARY OF INVENTION

Technical Problem

For the above-mentioned second method, further improvement has been demanded in the quality of the predicted mass-to-charge ratio database. For example, there is a possibility that the quality of the predicted mass-to-charge ratio database may be affected by low-quality genome data included in the genome database.

The present disclosure has been devised to overcome the above-described shortcoming, and an object is to enhance the quality of a mass-to-charge ratio database that is used in microbial identification based on mass spectrometry and that is constructed based on a genome database.

Solution to Problem

A method of constructing a microbial identification database according to a first aspect of the present disclosure comprises: acquiring genome data for microorganisms from a genome database; determining whether a criterion is satisfied by the genome data thus acquired; for respective sets of the genome data that were determined that they satisfied the criterion, predicting proteins to be expressed; and constructing a mass-to-charge ratio database including mass-to-charge ratio lists, the mass-to-charge ratio lists being predicted for the respective sets of the genome data based on the proteins thus predicted.

An apparatus configured to construct a microbial identification database according to a second aspect of the present disclosure constructs a microbial identification database by using genome data for microorganisms acquired from a genome database. The apparatus comprises a processor and a storage unit. The processor determines whether a criterion is satisfied by the genome data thus acquired. Moreover, the processor, for respective sets of the genome data that were determined that they satisfied the criterion, predicts proteins to be expressed. Moreover, the processor constructs a mass-to-charge ratio database including mass-to-charge ratio lists, the mass-to-charge ratio lists being predicted for the respective sets of the genome data based on the proteins thus predicted. Moreover, the processor stores the mass-to-charge ratio database in the storage unit.

Advantageous Effects of Invention

By employing the method of constructing a microbial identification database according to the present disclosure, it is possible to construct a mass-to-charge ratio database based solely on the genome data in a genome database that satisfies a criterion. In other words, it is possible to enhance the quality of a mass-to-charge ratio database that is used in microbial identification based on mass spectrometry and that is constructed based on a genome database.

DESCRIPTION OF EMBODIMENTS

Figure 1:
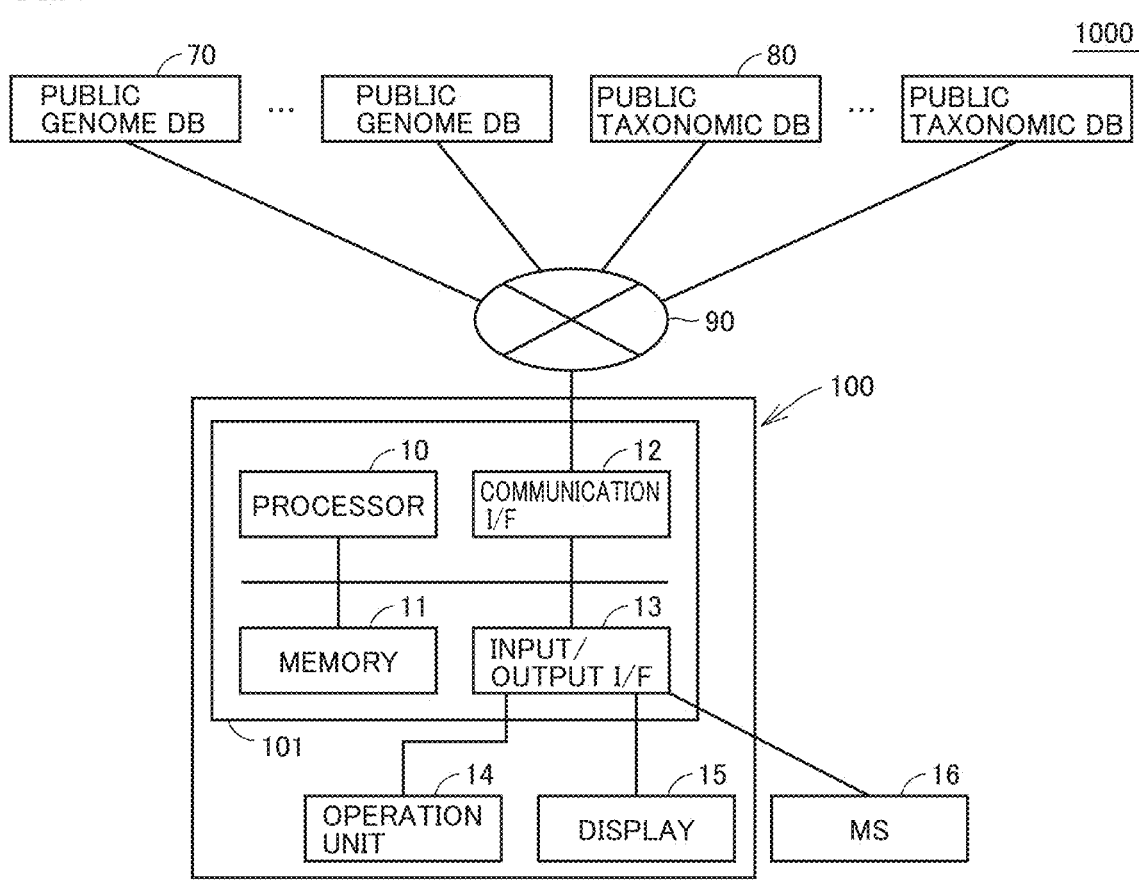
FIG. 1 is a schematic view illustrating the configuration of a microbial identification system according to an embodiment of the present invention.

In the following, a detailed description will be given of embodiments of the present invention, with reference to drawings. The same or corresponding portions in the drawings are denoted by the same reference characters, and basically, the description thereof is not repeated.

1. Configuration of Microbial Identification System

FIG. 1 is a schematic view illustrating the configuration of a microbial identification system 1000 according to an embodiment of the present invention.

Referring to FIG. 1, microbial identification system 1000 includes a public genome database 70, a public taxonomic database 80, a network 90, and an apparatus 100. Herein, "database" is also expressed as "DB".

Public genome DB 70 is a database that includes genome data for living things. A genome is a piece of genetic information on a nucleic acid (deoxyribonucleic acid (DNA), ribonucleic acid (RNA)) of a living thing, and it includes the base sequence of the nucleic acid. Herein, genome data mainly refers to DNA sequence data.

Public genome DB 70 is typically a publicly available DB that includes many genome data for living things, and, for example, it is a genome DB available from NCBI (National Center for Biotechnology Information), DDBJ (DNA Data Bank of Japan), and/or EMBL (European Molecular Biology Laboratory). Examples of public genome DB 70 are not limited to those mentioned above, and, for example, a genome DB that is not publicly available may also be included.

Public taxonomic DB 80 is a database that includes data about taxonomy of living things (hereinafter, such data is referred to as taxonomic data). Generally, taxonomy of living things refers to a taxonomy based on the relatedness between living things defined by classes such as family, genus, and species. Traditionally, classification in microbial taxonomy is based on both the phenotypes and the genomes and it is on the basis of a plurality of indexes such as morphology observation, phenotypes, chemotaxonomic indexes, protein analysis, and DNA analysis, but there are a plurality of taxonomic systems including a taxonomic system solely based on genomic information.

Public taxonomic DB 80 is typically a publicly available DB that includes taxonomic data of living things, and, for example, it is a DB such as GTDB (Genome Taxonomy Database), RDP (Ribosomal Database Project), and/or Silva. Examples of public taxonomic DB 80 are not limited to those mentioned above, and, for example, a DB that is not publicly available may also be included.

Network 90 is a network for communication between apparatus 100 and both the public genome DB 70 and the public taxonomic DB 80. For example, network 90 is the Internet that interconnects many government-owned, corporate-owned, public, and private networks present on the earth.

Apparatus 100 is an apparatus that constructs a mass-to-charge ratio (m/z) DB for use to identify microorganisms by mass spectrometry. Herein, identifying a microorganism refers to taxonomically identifying the microorganism. More specifically, it refers to identifying at least one of the genus, species, strain, and phylogenetic group of the microorganism, for example. Hence, apparatus 100 corresponds to an example of the "apparatus that constructs a database for use to identify microorganisms". Moreover, apparatus 100 is also an apparatus for identifying microorganisms by mass spectrometry with the use of the m/z DB. Hence, apparatus 100 also corresponds to an example of the "microbial identification apparatus". Herein, the "type" of microorganisms or living things includes at least one of "the genotype, the strain, and the rank in the phylogenetic taxa such as subspecies, species, genus, and/or family" of the microorganisms or living things, for example.

Apparatus 100 includes a controller 101, a display 15, and an operation unit 14. Display 15 and operation unit 14 are connected to controller 101. Operation unit 14 is typically configured with a touch panel, a keyboard, a mouse, and/or the like. Operation unit 14 receives operation inputs that a user makes to a processor 10. Display 15 is configured with a liquid crystal panel capable of displaying images, for example. Display 15 displays an image related to receipt of an operation input from the user, and also displays results of the process performed by processor 10.

Controller 101 has processor 10, a memory 11, a communication interface (I/F) 12, and an input/output I/F 13, as its main components. These units are communicatively connected with one another via a bus.

Processor 10 is typically an arithmetic processing unit such as a CPU (Central Processing Unit) or an MPU (Micro Processing Unit). Processor 10 controls the operation of apparatus 100 by reading and executing a program stored in memory 11.

Memory 11 is implemented by a storage apparatus such as a ROM (Read Only Memory), a RAM (Random Access Memory), and an HDD (Hard Disk Drive), for example. A ROM is capable of storing a program that is to be executed by processor 10. A RAM is capable of temporarily storing data that is to be used by processor 10 during execution of a program, and functioning as a temporary data memory used as a work area. An HDD is a non-volatile storage apparatus. In addition to an HDD or instead of an HDD, a semiconductor storage apparatus such as a flash memory may be adopted. The program and/or data may be stored in an external storage apparatus that is accessible by processor 10. Memory 11 corresponds to an example of a "storage unit".

Communication I/F 12 is a communication interface for exchanging various data with an external apparatus including public genome DB 70 and public taxonomic DB 80, and is configured by an adaptor, a connector, or the like. The mode of communication may be wireless communication via wireless LAN (Local Area Network) and/or the like, or may be wired communication with the use of an USB (Universal Serial Bus) and/or the like.

Input/output I/F 13 is an interface for exchanging various data between processor 10 and an external device that is connected to input/output I/F 13. The external device includes operation unit 14 and display 15. To input/output I/F 13, a mass spectrometry apparatus (MS) 16 may be connected. Herein, input/output I/F 13 also includes a device that exchanges data between a storage terminal connected to apparatus 100, such as a USB memory, and processor 10.

MS 16 is an apparatus for performing mass spectrometry of components of a sample, and examples thereof include, but are not limited to, MALDI-TOF MS (Matrix-Assisted Laser Desorption/Ionization Time-of-Flight Mass Spectrometry), MALDI-IT-TOF (Matrix-Assisted Laser Desorption/Ionization Ion Trap Time-of-Flight Mass Spectrometry), and scanning IT-MS. In the case when MS 16 is MALDI-TOF MS, it makes ions, which are generated by laser irradiation, enter into a flight tube, flies them to separate them from each other according to the time of flight, and then detects them. The time of flight correlates with the mass-to-charge ratio, m/z, of the component. As a result, a mass spectrum is obtained which has the m/z on the horizontal axis and the detected ionic strength on the vertical axis.

Herein, MS 16 performs mass spectrometry of proteins in a sample. As a result, on the mass spectrum, peaks are detected for the m/z values of the proteins in the sample. So, by referencing to the pattern of the mass spectrum, more specifically, by referring to a list of m/z values for peaks as high as or higher than a certain threshold value (herein also called an m/z list), it is possible to understand what proteins are included in the sample. Herein, an m/z (value) in an m/z list refers to an m/z (value) for a peak on a mass spectrum.

Different types of living things include different proteins, and, accordingly, they exhibit different mass spectrum patterns and different m/z lists. Because of this, it is possible to identify a living thing based on the mass spectrum pattern and the m/z list.

After performing mass spectrometry of an unknown microorganism, which is the sample, MS 16 sends a sample list, which is the m/z list for the sample, to apparatus 100. Based on the sample list, processor 10 identifies the sample.

Apparatus 100 is not necessarily configured with one computer, and it may be configured with a plurality of computers.

2. Comparison with Conventional Apparatus

Conventionally, as such a microbial identification method using a mass spectrometry apparatus, a fingerprinting method has been employed which involves constructing a database that includes mass spectra actually measured for microorganisms and comparing the database with a mass spectrum for an unknown microorganism.

However, in order to construct a practical database usable for a fingerprinting method, it is necessary to obtain mass spectrum data actually measured for many types of microorganisms (well over a thousand types, for example). Moreover, the mass spectrum pattern for the same type of microorganisms can vary due to variations in genetic diversity, incubating conditions, pretreatment performed prior to mass spectrum measurement, and repeated measurements. Accordingly, in light of these circumstances, to obtain a practical database, numerous mass spectrum data is required; for example, several dozen mass spectrum data is required for each type of microorganisms, so a total of tens of thousands of mass spectrum data is required for all types of microorganisms. This means that for constructing a practical database, actual microbial incubation and mass spectrum measurement need to be performed numerous times (tens of thousands of times, for example), which requires numerous money.

To address this problem, as a new microbial identification method using mass spectrometry, a method has been receiving attention that involves using a public genome database to predict proteins that can be potentially expressed, constructing an m/z DB which is a database of m/z lists predicted from these proteins, and using the m/z DB. In this method, the m/z lists included in the m/z DB are compared with a sample list which is an m/z list corresponding to peaks on a mass spectrum for an unknown microorganism, for identification of the sample. This method does not require actually performing microbial incubation or mass spectrum measurement, so is capable of constructing a mass spectrum database in an easy and simple manner as compared to the above-mentioned fingerprinting method.

However, this method still has room for improvement in the quality of the predicted m/z DB and also in the accuracy of microbial identification performed by using the m/z DB.

For example, in this method, low-quality genome data included in a public genome database (for example, genome data that includes many undetermined bases) is also reflected in the m/z DB. This lowers the quality of the m/z DB, and accordingly, lowers the accuracy of microbial identification using the m/z DB, which is a problem.

To address this problem, in apparatus 100 according to the present embodiment, an m/z DB is constructed based solely on high-quality genome data that satisfies certain criteria, among all the genome data acquired from public genome DB 70. This makes it possible to enhance the quality of the m/z DB. It also makes it possible to enhance the accuracy of microbial identification using the m/z DB.

Furthermore, a conventional microbial identification method using a predicted m/z DB has another problem. For example, the predicted m/z lists can include a false peak which does not appear on an actually-measured mass spectrum. More specifically, a peak may not be detected on an actually-measured mass spectrum when a sequence in the genome data is predicted to express a protein but actual expression of the protein does not occur due to some cause, or when a protein is expressed but not ionized. As a result, at the time when the sample list is compared with the predicted m/z lists, the false peak can serve as noise and, thereby, the sample list can end up matching with an m/z list that is for a type of microorganism not related to the sample. In this case, the sample can be identified as a microorganism that is not related thereto. That is, the accuracy of microbial identification can be lowered, which is a problem.

To address this problem, in apparatus 100 according to the present embodiment, microbial identification is performed with weights assigned to proteins that are unlikely to appear as false peaks, namely, "proteins that are highly likely to be expressed in living microorganisms and highly likely to be detected as peaks at the time of mass spectrum measurement". This decreases the possibility of falsely identifying as a wrong microorganism due to false peaks. Thus, it can enhance the accuracy of microbial identification.

3. Outline of Processes Performed at Apparatus

Figure 2:
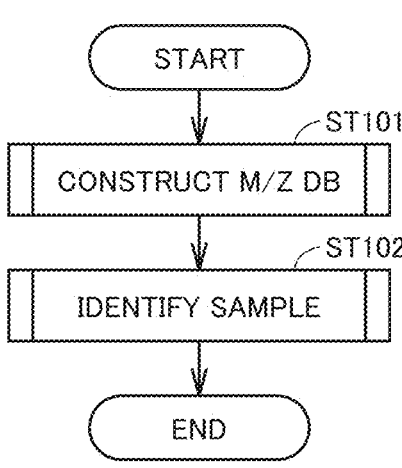
FIG. 2 is a flowchart illustrating the outline of the processes performed at an apparatus.

FIG. 2 is a flowchart illustrating the outline of the processes performed at apparatus 100. In a step (hereinafter also referred to as ST) 101, processor 10 of apparatus 100 constructs an m/z DB from genome data in public genome DB 70. In ST102, processor 10 identifies a sample which is an unknown microorganism by using the m/z DB.

(3-1. Functional Block Related to Construction of m/z DB)

Figure 3:
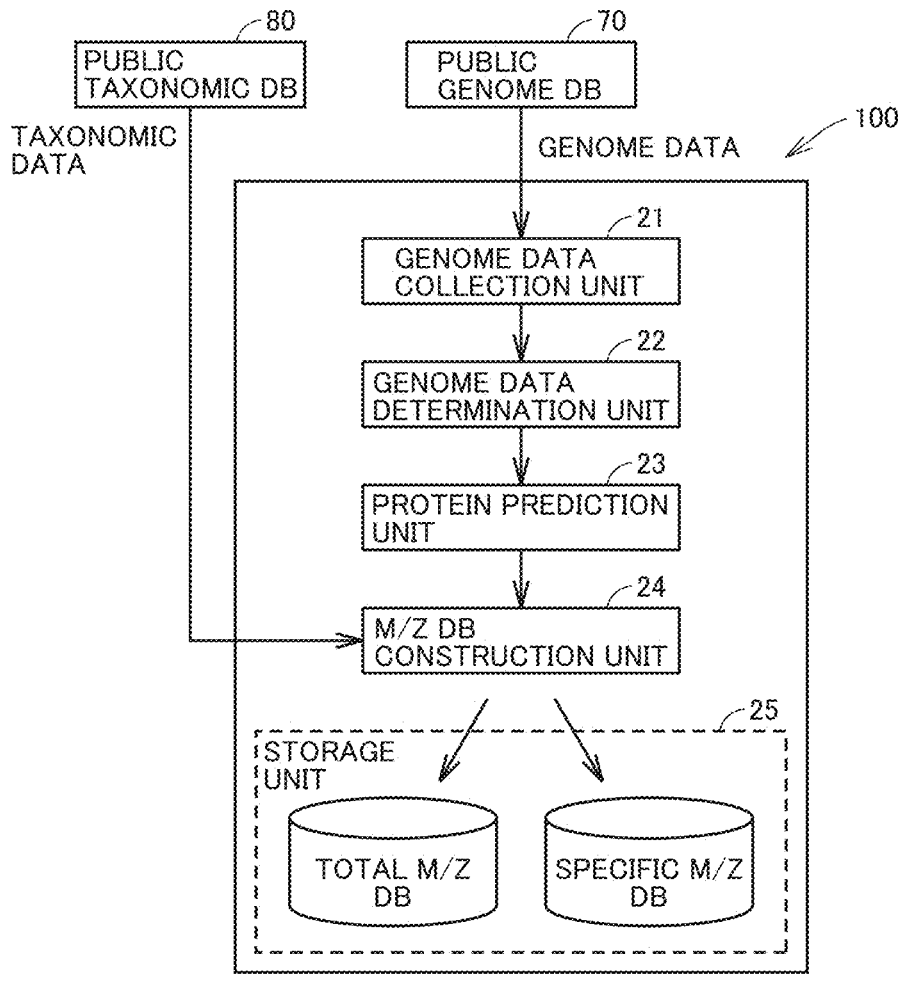
FIG. 3 is a functional block diagram of an apparatus, related to construction of a mass-to-charge ratio database.

FIG. 3 is a functional block diagram of apparatus 100, related to construction of an m/z DB corresponding to ST101 in FIG. 2. Referring to FIG. 3, apparatus 100 includes a genome data collection unit 21, a genome data determination unit 22, a protein prediction unit 23, an m/z DB construction unit 24, and a storage unit 25.

Genome data collection unit 21 collects genome data from public genome DB 70.

Genome data determination unit 22 determines whether the genome data thus collected satisfies certain criteria that are associated with the quality of the genome data.

As for the genome data that satisfied the certain criteria, protein prediction unit 23 predicts proteins to be expressed. More specifically, it predicts an estimated gene region from the DNA sequence, and predicts an amino acid sequence from the estimated gene region. Then, based on the amino acid sequence, it predicts a protein to be expressed.

Based on the proteins thus predicted, m/z DB construction unit 24 predicts m/z lists, constructs an m/z DB, and stores in storage unit 25. The m/z DB includes two types of m/z DBs, for example. One of the m/z DBs is a total m/z DB that includes m/z values for all the proteins predicted from the genome data. The other m/z DB is a specific m/z DB that only includes m/z values for proteins included in a specific group, among the proteins predicted from the genome data. These two m/z DBs are used for identification of the sample, which is an unknown microorganism, described in FIG. 4.

Genome data collection unit 21, genome data determination unit 22, protein prediction unit 23, and m/z DB construction unit 24 correspond to processor 10 in FIG. 1. Storage unit 25 corresponds to memory 11 in FIG. 1.

(3-2. Functional Block Related to Identification of Sample)

Figure 4:
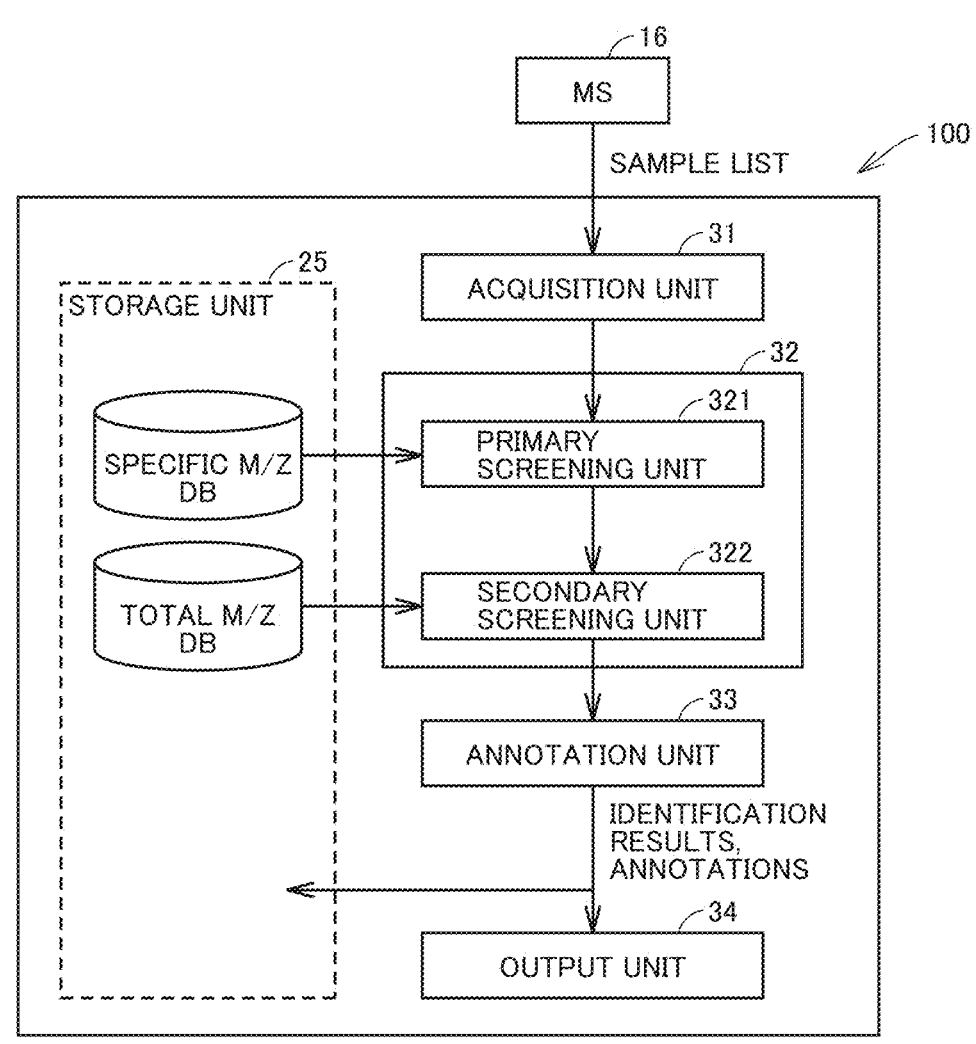
FIG. 4 is a functional block diagram of an apparatus, related to identification of a sample.

FIG. 4 is a functional block diagram of apparatus 100, related to identification of a sample corresponding to ST102 in FIG. 2. Referring to FIG. 4, apparatus 100 includes an acquisition unit 31, a sample identification unit 32, an annotation unit 33, an output unit 34, and storage unit 25.

Acquisition unit 31 acquires a sample list. The sample list is acquired from MS 16 connected to apparatus 100, for example. The method for acquiring the sample list is not limited to the above-mentioned one, and, for example, the sample list may be acquired from an external apparatus that is in communication with apparatus 100, or from a storage terminal that is connected to apparatus 100. Further, as needed, acquisition unit 31 estimates a measurement error of the m/z values included in the sample list and corrects it. Acquisition unit 31 corresponds to processor 10 in FIG. 1.

Sample identification unit 32 identifies the sample by comparing the sample list with the m/z DB stored in storage unit 25, with weights assigned to m/z values for proteins included in a specific group. Sample identification unit 32 includes a primary screening unit 321 and a secondary screening unit 322, for example. Primary screening unit 321 uses m/z lists included in the specific m/z DB, to perform screening based on the m/z values for the proteins included in the specific group. Among the m/z lists included in the total m/z DB, for the m/z lists corresponding to the genome data selected by the primary screening, secondary screening unit 322 performs screening based on the m/z values for all the proteins, to identify the sample. Sample identification unit 32 corresponds to processor 10 in FIG. 1.

Annotation unit 33 links an annotation, which is a piece of information regarding a predicted protein, to each m/z included in the sample list. For linking the annotation, software capable of retrieving a corresponding protein name based on protein mass is used, for example. Annotation unit 33 corresponds to processor 10 in FIG. 1.

Results of identification performed by sample identification unit 32 as well as m/z annotations are stored in storage unit 25 and/or output by output unit 34. Output unit 34 corresponds to processor 10 and either display 15 or communication I/F 12 in FIG. 1. In other words, results of identification and annotations are displayed on display 15, and/or sent to an external apparatus via communication I/F 12. As a result, a user can recognize the results of identification and the annotations.

4. Flow of Processes Related to Construction of m/z DB (4-1. Construction of m/z DB)

In the following, the flow of the processes performed at apparatus 100 will be described more specifically.

Figure 5:
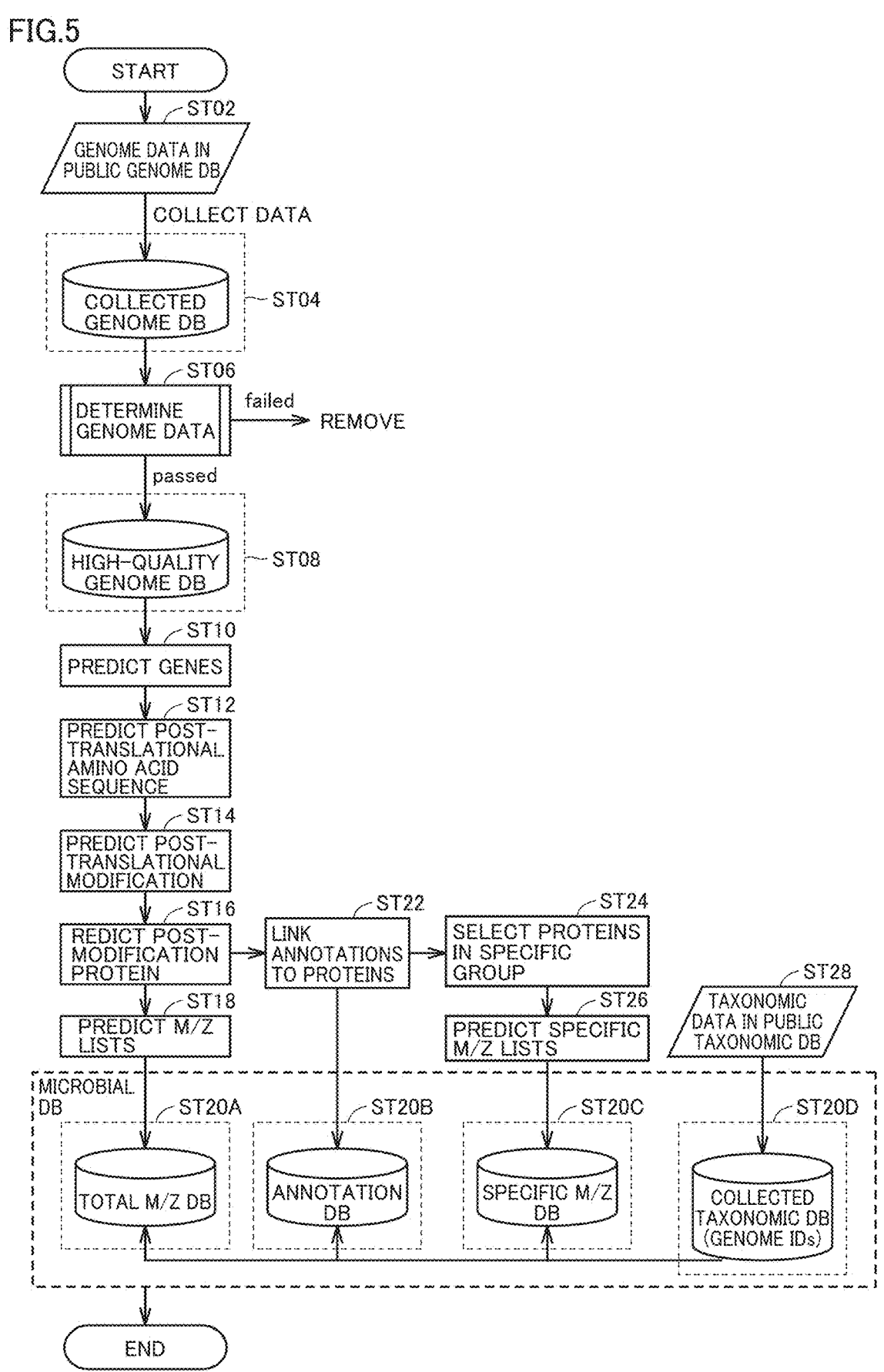
FIG. 5 is a flowchart illustrating the processes for constructing a mass-to-charge ratio database.

FIG. 5 is a flowchart illustrating the processes for constructing an m/z DB. The processes from ST02 to ST28 illustrated in FIG. 5 correspond to the process of ST101 in FIG. 2.

Referring to FIG. 5, in ST02, processor 10 acquires genome data for microorganisms from public genome DB 70. At this point, by acquiring genome data from a plurality of public genome DBs 70, it is possible to exhaustively collect genome data related to clinically or industrially important microbial species.

In ST04, processor 10 combines the acquired genome data together to construct a collected genome DB.

In ST06, processor 10 determines whether the genome data in the collected genome DB satisfies criteria that are determined in advance. The criteria are set so that only high-quality genome data satisfies the criteria. Details of the criteria are to be described in FIG. 6.

In ST08, processor 10 constructs a high-quality genome DB that includes the genome data that was determined that they satisfied the criteria.

In ST10, as for the genome data included in the high-quality genome DB, processor 10 predicts genes that are included in the genome data. A gene refers to a particular region of DNA that is to be translated into a protein, or information included at the region. For example, the prediction of the gene includes estimating, in the genome data, an estimated gene region that is to be translated into a protein, by using a translation start codon (ATG sequence) and a stop codon (TGA sequence).

In ST12, processor 10 predicts an amino acid sequence to be translated from the predicted gene. For example, the prediction of the amino acid sequence includes estimating amino acids corresponding to respective codons (three-base sequences) included in the estimated gene region and joining them together.

In ST14, processor 10 predicts post-translational modification to which a protein made up from the predicted amino acid sequence can be subjected to. Post-translational modification is a modification to which a protein is subjected immediately after translation, for altering the protein into a functional protein that functions at designated locations in the actual living body. Examples of post-translational modification include breaking-down of the protein including methionine removal and signal peptide removal, as well as specific chemical modification including phosphorylation. Post-translational modification occurs to almost all proteins to alter their m/z values. Therefore, by taking post-translational modification into consideration, it is possible to calculate protein m/z values with more accuracy.

In ST16, processor 10 predicts a protein that includes the predicted post-translational modification.

In ST18, based on the resulting proteins, processor 10 predicts m/z lists for respective sets of genome data. More specifically, based on the masses of the atoms included in each protein, m/z values for the protein are calculated. As the mass of each atom, the average mass of the element reflecting the isotope distribution of the element in nature is preferably used. By this, a more accurate m/z is calculated.

In ST20A, processor 10 constructs a total m/z DB, which is a mass-to-charge ratio database that includes the m/z lists. The total m/z DB includes all m/z values predicted for respective sets of the genome data.

Meanwhile, in ST22, processor 10 links an annotation to the data related to each protein predicted in ST16. An annotation is, in general, a piece of information regarding a protein, and it includes protein name, function, and the like. The linking of the annotation is performed by using a widely-used software capable of adding an annotation to a corresponding m/z, for example, but this is not limitative; it may be performed by, for example, using a table that shows the relationship between m/z values and annotations, created by apparatus 100 based on public genome DB 70 and public taxonomic DB 80.

Herein, the annotation is a piece of information regarding the protein, and it includes information regarding a group in which the protein is included. Information regarding a group for the protein includes at least one of protein name, function, and family.

An advantage of linking annotations is that it makes it possible to select m/z values for proteins included in a specific group based on the annotations, and thereby treat these m/z values separately from m/z values for other proteins. Thereby, for example, it is made possible to perform identification of a microorganism with weights selectively assigned to m/z values for "a group of proteins that are highly likely to be expressed in living microorganisms and highly likely to be detected as peaks at the time of mass spectrum measurement". As a result, it is made possible to identify the sample with weights assigned to "m/z values for proteins that are highly likely to be expressed in a living thing and highly likely to be detected as peaks at the time of mass spectrum measurement" in the m/z lists predicted from genome data, against "m/z values for proteins that are not expressed in actual living microorganisms or proteins that are expressed but not appear on the mass spectrum (false peaks)". Thus, it is made possible to inhibit false peaks included in the predicted m/z lists from appearing as noise and lowering the accuracy of sample identification.

To be "highly likely to be expressed in a living thing and detected as peaks at the time of mass spectrum measurement", the group is preferably selected based on at least one of the following criteria: a criterion that an expression amount is equal to or more than a certain threshold value; a criterion that a vital function is possessed; a criterion that at least a certain proportion of microorganisms among microorganisms that are classified as a certain type (for example, microorganisms that belong to a certain family) share a degree of amino acid sequence similarity (homology) equal to or more than a certain threshold value; a criterion that each of the proteins is a basic protein; a criterion that a margin of error of mass-to-charge ratio analysis by MALDI-MS measurement is ±14 Da (further preferably ±3 Da); a criterion that each of the proteins has a mass from 4 to 30 kDa (further preferably from 2 to 20 kDa); a criterion that the group includes at least a certain number of types of proteins; and a criterion that at least a certain proportion of microorganisms among microorganisms that are classified as a certain type (for example, microorganisms that belong to a certain family) include the genome data.

The vital function includes a function essential for at least one of cell maintenance and cell growth.

An example of a group that is determined in light of these criteria is a group of ribosomal proteins. Other examples are a group of chaperones and a group of DNA-binding proteins.

Moreover, the group is not particularly limited to the above-mentioned proteins noticeably expressed universally in microorganisms in general, but it may also be proteins that are known to be noticeably expressed in particular microorganisms. For example, by performing identification of the sample with weights assigned to particular proteins that are known to be noticeably expressed in respective genera, it is possible to enhance the possibility of successful identification of the right genus of the sample. An example of the "noticeably expressed proteins" herein is a protein the expression amount of which is equal to or more than a certain threshold value.

In ST24, based on the group-related information included in the annotations, processor 10 selects proteins that are predicted to be included in a specific group. Subsequently, in ST26, processor 10 predicts specific m/z lists that include only the m/z values predicted from the selected proteins. In ST20C, processor 10 constructs a specific m/z DB that is an m/z database including the specific m/z lists.

Another advantage of linking annotations is that it makes it easy for a user to understand respectively what type of proteins the m/z values included in the m/z lists correspond to. From this viewpoint, in order to make it easier to use annotations corresponding to m/z values, in ST20B, processor 10 constructs an annotation DB that includes all the annotations corresponding to the m/z values included in the total m/z DB.

Yet another advantage of linking annotations is that referencing to the annotations makes it possible to evaluate the validity of comparing the sample list with the m/z lists included in the m/z DB. For example, when an m/z list in the m/z DB is determined that the degree of matching (the matching rate) with the sample list is high in terms of the m/z pattern, a reference can be made to its annotation. Then, if the m/z list includes many m/z values for proteins that are not estimated, according to the annotation, to be expressed in the microorganism, the m/z list may be not very reliable, so the validity of comparing it with the sample list is low and also the reliability of sample identification is low. Moreover, if an m/z in the sample list that is for a protein considered to be functionally important and evolutionarily conserved is the same as an m/z for noise in the m/z list, the validity of comparison is low and also the reliability of sample identification is low. When an m/z list is found to be poorly valid to comparison with the sample list, a user can take an action, such as removing the m/z list, to enhance the reliability of the identification.

The annotations in the annotation DB are linked to the m/z values included in the m/z DB. In an example, the m/z DB and the annotation DB are associated to each other so that at the time when reference is made to the m/z values in the m/z lists included in the m/z DB, reference can also be made to the corresponding annotations included in the annotation DB. In another example, the annotation DB may be configured as a part of the m/z DB, in such a manner that annotations are added to corresponding m/z values in the m/z DB.

In ST28, processor 10 acquires taxonomic data from public taxonomic DB 80. In ST20D, processor 10 constructs a collected taxonomic DB that combines taxonomic data thus collected. At this time, by constructing the collected taxonomic DB based on taxonomic data from a plurality of public taxonomic DBs 80, it is possible to incorporate a wide range of taxonomic systems. In this way, by using the collected taxonomic DB, it is possible to reflect a variety of taxonomic systems in microbial identification results.

Moreover, the collected taxonomic DB may also include genome IDs which are IDs for respective genomes. The genome IDs are created based on the taxonomic data thus collected, for example.

The taxonomic data in the collected taxonomic DB is brought into association with data included in the total m/z DB, the specific m/z DB, and the annotation DB. By this, it is made possible to add genome IDs to both the genome data in the total m/z DB as well as the genome data in the specific m/z DB. It is also possible to use the content of the collected taxonomic DB for organizing the total m/z DB and the specific m/z DB, and/or to reflect the content of the former DB in the content of the latter DBs. In addition, it is also possible to use the collected taxonomic DB for other purposes in apparatus 100, such as for determining the above-mentioned "particular proteins that are known to be noticeably expressed in a particular species".

These four DBs associated together are referred to as a microbial DB. After constructing the microbial DB in ST20A to 20D, processor 10 pauses the process. This allows apparatus 100 to use the microbial DB to perform sample identification with the use of mass spectrometry, which is to be described in detail in FIG. 8 and FIG. 9.

The processes illustrated in FIG. 5 are performed, for example, once a year, at the time of update of public genome DB 70, for example. As a result of this, the updated content of public genome DB 70 can be properly reflected in the microbial DB, and thereby the content of the microbial DB is further improved.

(4-2. Determination of Genome Data)

Figure 6:
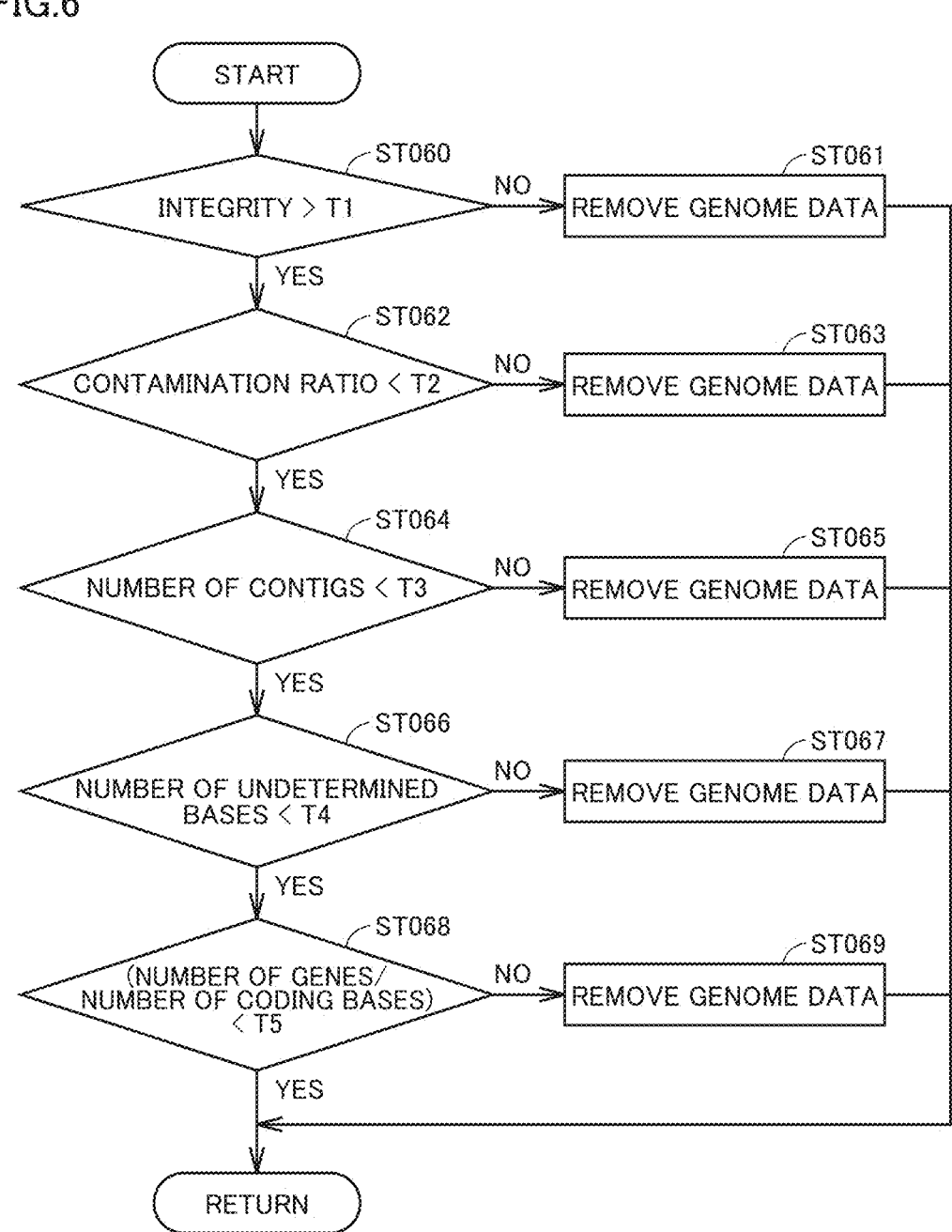
FIG. 6 is a flowchart illustrating a subroutine for genome data determination.

FIG. 6 is a diagram illustrating the processes for genome data determination. The processes ST060 to ST069 in FIG. 6 correspond to ST06 in FIG. 2. The processes illustrated in FIG. 6 are performed for removing low-quality genome data included in the collected genome DB.

In ST060, processor 10 determines the quality of the genome data based on the integrity of the genome data. For example, integrity of a genome is determined by using, as an index, a group of single copy marker genes, each of which is known to be present one copy in every microbial genome. When the genome data is of integrity, all the single copy marker genes should be present in the sample. However, when the genome data is not of integrity, such as, for example, when a part of the genome data is lost or misread, a single copy marker gene included in the lost part is not present. Therefore, the greater the lost part or the misread part of the genome data, the fewer the number of single copy marker genes in the genome data. For this reason, the number of single copy marker genes can be used as an index of the integrity of the genome data. More specifically, integrity is calculated as a proportion of the number of single copy marker genes that are actually present, relative to the number of all the single copy marker genes that can be possibly present in the genome data, the latter being defined as 100%.

More specifically, in ST060, processor 10 determines whether the integrity of the genome data is more than a reference value T1. For example, reference value T1 is 50%. When the integrity is equal to or less than reference value T1 (when NO in ST060), in ST061, processor 10 removes the genome data. When the integrity is more than reference value T1 (when YES in ST060), processor 10 proceeds the process to ST062.

In ST062, processor 10 determines the quality of the genome data based on the contamination ratio of the genome. Contamination refers to a phenomenon where the DNA sequence of one set of genome data is mixed with the DNA sequence of another set of genome data for some cause. In other words, contamination typically refers to a state where the DNA sequences of a plurality of microorganisms are mixed together. When the ratio of single copy marker genes under no genome data contamination is defined as 100%, the ratio under contamination is more than 100%. Therefore, for example, the contamination ratio is calculated based on the number of single copy marker genes that are actually found, with the ratio of all the single copy marker genes possibly present in the genome data under no contamination being defined as 100%. When the number of single copy marker genes that are actually found corresponds to (100+n) %, the contamination ratio is n %. n is a real number that satisfies n>0. When the contamination ratio is high, it is highly likely that the DNA sequences of a plurality of types of microorganisms are mixed together.

More specifically, in ST062, processor 10 determines whether the contamination ratio is less than a reference value T2. For example, reference value T2 is 20%. When the contamination ratio is equal to or more than reference T2 (when NO in ST062), in ST063, processor 10 removes the genome data. When the contamination ratio is less than reference value T2 (when YES in ST062), processor 10 proceeds the process to ST064.

In ST064, processor 10 determines the quality of the genome data based on the number of contigs. When a DNA sequence which is intrinsically present as one piece is divided into a plurality of DNA sequence segments, each of the sequence segments is referred to as a contig. Therefore, the greater the number of contigs, the smaller the segments of the DNA sequence. When the number of contigs is too high, there is a possibility that a gene region to be expressed into a protein can be divided, potentially making it impossible to perform proper reading. The number of contigs can be known by counting the number of segments of the DNA sequence included in the genome data.

More specifically, in ST064, processor 10 determines whether the number of contigs is less than a reference value T3. For example, reference value T3 is 1000. When the number of contigs is equal to or more than reference value T3 (when NO in ST064), in ST065, processor 10 removes the genome data. When the number of contigs is less than reference value T3 (when YES in ST064), processor 10 proceeds the process to ST066.

In ST066, processor 10 determines the quality of the genome data based on the number of undetermined bases. An undetermined base refers to a base that was not determined as any of A, G, C, and T at the time of DNA sequencing. From a DNA sequence that includes many undetermined bases, proper reading of the genes is highly likely impossible.

More specifically, in ST066, processor 10 determines whether the number of undetermined bases is less than a reference value T4. For example, reference value T4 is 100,000. When the number of undetermined bases is equal to or more than reference value T4 (when NO in ST066), in ST067, processor 10 removes the genome data. When the number of contigs is less than reference value T4 (when YES in ST067), processor 10 proceeds the process to ST068.

In ST068, processor 10 determines the quality of the genome data based on whether the number of genes satisfies a reference value. This reference is set for the purpose of determining whether the number of genes estimated from the genome data is within a proper range. For example, when the number of genes estimated from the genome data is too high, it is conceivable that a moiety that is actually not a gene is estimated as a gene for some cause. The some cause refers to a case when due to, for example, an error in DNA sequencing, a sequence that is not related to a start, or a stop, of transcription or translation is misread as a sequence that is related to a start, or a stop, of transcription or translation. In this case, a sequence that is not to be expressed into a protein is misread as a sequence that is to be expressed into a protein, and thereby many wrong peaks can be included in the predicted m/z lists. When such an m/z list is included in the m/z DB, the quality of the m/z DB is low, and accordingly, the accuracy of sample identification is also low.

More specifically, in ST068, processor 10 determines whether the number resulting from division of the number of genes in the genome data by the number of coding bases is less than a reference value T5. Generally, a coding base refers to a base that is included in a region of a DNA sequence related to protein expression. For example, reference value T5 is 0.00180. When the above-mentioned number obtained by division is equal to or more than reference value T5 (when NO in ST068), in ST069, processor 10 removes the genome data. When the above-mentioned number obtained by division is less than reference value T5 (when YES in ST068), processor 10 adds the genome data to the high-quality genome DB.

Processor 10 performs ST060 to ST069 to the entire genome data included in the collected genome DB.

It should be noted that the method of calculation for each of the criteria including the integrity, the contamination ratio, the number of contigs, the number of undetermined bases, and the validity of the number of genes is not limited to the above-described examples. For example, the validity of the number of genes may be determined based on whether the number of genes included in one set of genome data is less than a certain reference value.

By the processes illustrated in FIG. 6, genome data included in the collected genome DB and failing to satisfy the criteria is removed. More specifically, among the genome data included in public genome DB 70, low-quality one is removed, and only the high-quality one is used for constructing the m/z DB. As a result, the quality of the m/z DB in apparatus 100 is enhanced.

(4-3. Addition of New Genome Data)

Apparatus 100 is further configured to be capable of adding new genome data to the m/z DB. The addition is performed when, for example, a user of apparatus 100 finds a new microorganism and desires to add genome data related to the microorganism.

Figure 7:
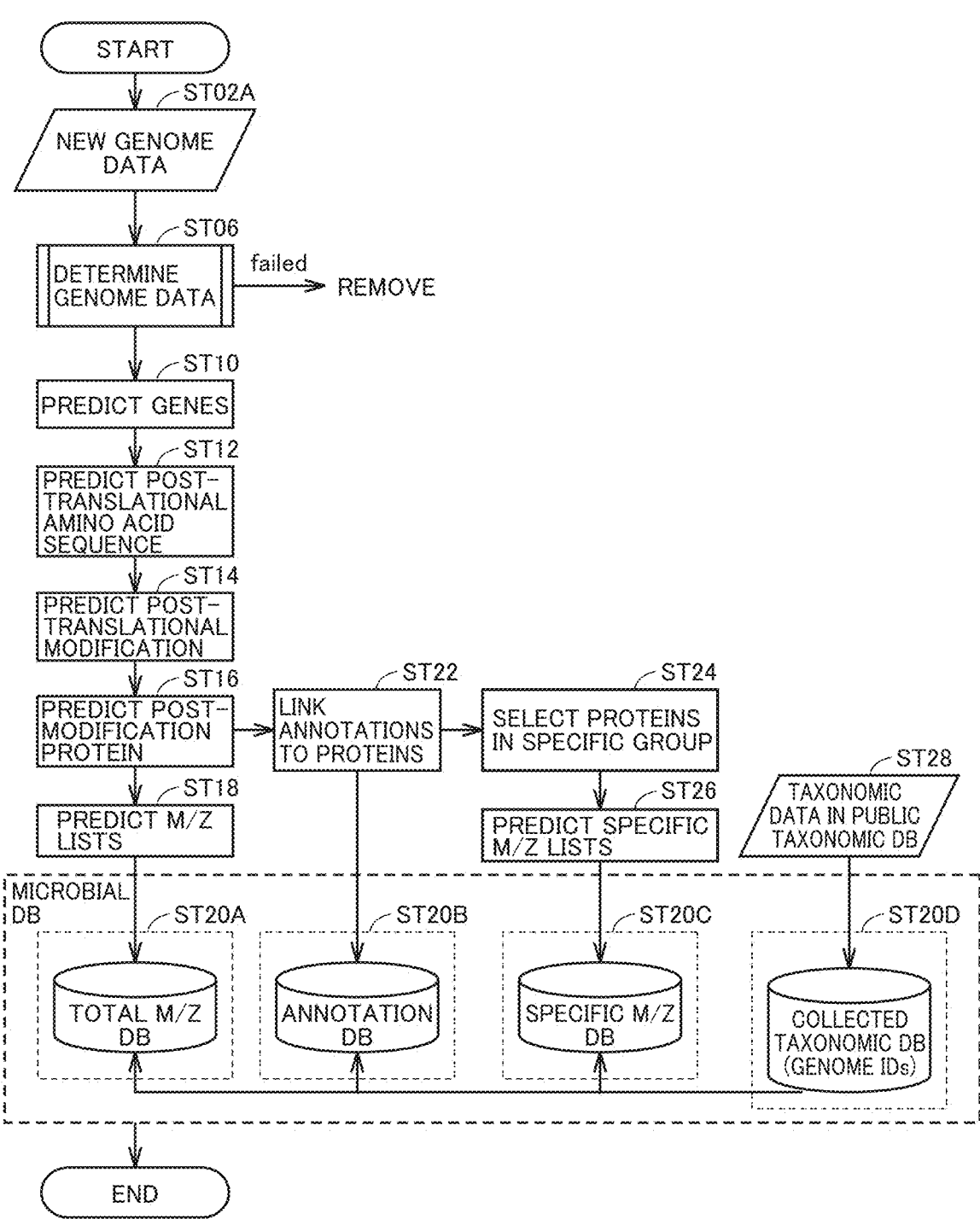
FIG. 7 is a flowchart illustrating the processes for adding new genome data.

FIG. 7 is a diagram illustrating the processes for adding new genome data. The flowchart in FIG. 7 differs from the flowchart in FIG. 5; ST02 is changed to ST02A, and steps ST04 and ST08 in FIG. 5 are deleted. The processes from ST12 onward in the flowchart in FIG. 7 correspond to the processes from ST12 onward in the flowchart in FIG. 5.

In ST02A, processor 10 acquires new genome data. More specifically, for example, processor 10 acquires the genome data either from an external apparatus such as a DNA sequencer or a storage apparatus, or from a storage terminal such as a USB memory, via input/output I/F 13 or communication I/F 12.

In ST06, processor 10 determines whether the genome data satisfies criteria. The criteria are set so that only high-quality genome data can satisfy the criteria. When the new genome data satisfies the criteria, processor 10 proceeds the process to ST10. When the new genome data fails to satisfy the criteria, processor 10 removes the new genome data.

In ST10, processor 10 predicts genes included in the genome data, and proceeds the process to ST12. The processes from this point onward are the same as those in FIG. 5, so the description thereof is not repeated. Thus, as for proteins that are predicted to be expressed according to the new genome data, processor 10 can add those to the m/z DB when the quality thereof satisfies certain criteria.

With the above-described configuration, it is possible to add, to the m/z DB, an m/z list predicted from newly-acquired genome data, and, thereby, it is possible to further enrich the content of the m/z DB. As a result, the quality of the m/z DB is further enhanced, and the accuracy of sample identification using the m/z DB is also further enhanced.

5. Flow of Processes Related to Identification of Sample (5-1. Two-Step Screening)

Apparatus 100 performs identification of the sample by using the m/z DB constructed in the above-described manner.

Figure 8:
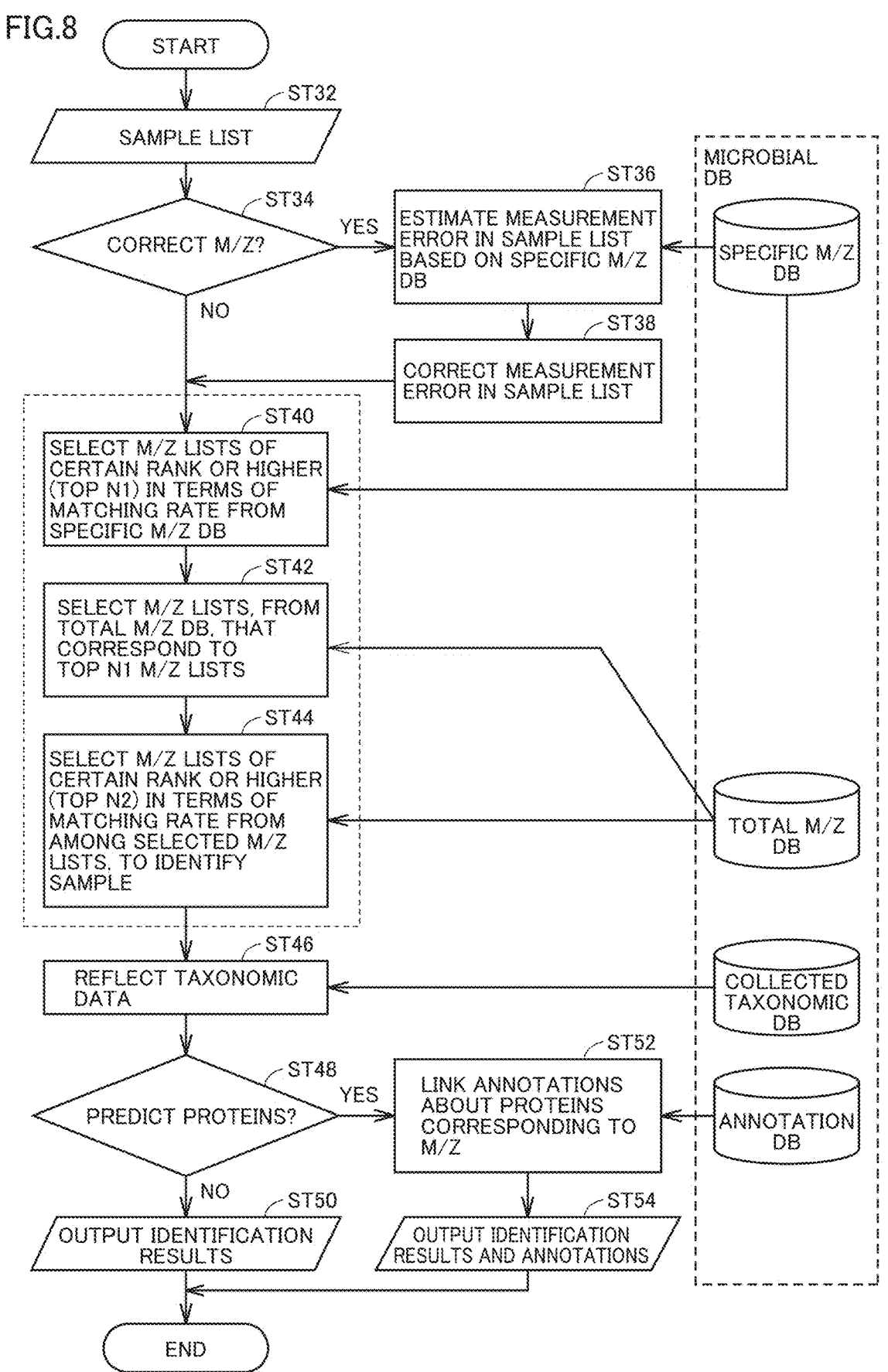
FIG. 8 is a flowchart illustrating the processes related to identification of a sample.

FIG. 8 is a flowchart illustrating the processes related to identification of a sample. The processes ST32 to ST54 illustrated in FIG. 8 correspond to ST102 in FIG. 2.

Referring to FIG. 8, in ST32, processor 10 acquires a sample list. The sample list is acquired from MS 16, for example. In ST34, processor 10 determines whether or not to correct the m/z values in the sample list. Whether or not to correct the sample list is set in advance by a user, for example.

In analysis that is performed by a mass spectrometry apparatus such as MALDI-TOF MS, depending on the mass of the proteins included in a sample and the apparatus used, for example, there is a possibility that an m/z smaller or greater than the actual value can be detected. That is, a sample list may have some degree of m/z shift as a measurement error. On the other hand, the m/z DB included in apparatus 100 is composed of theoretical values, so it is free of measurement errors. Therefore, by shifting the m/z values in the sample list so as to cancel measurement errors prior to comparing with the m/z DB included in apparatus 100, it is possible to perform sample identification with better accuracy.

Estimation of measurement errors is performed by the procedure described below. Firstly, the sample list, as it is, including a measurement error is compared with "an m/z list that is assumed to be (substantially) free of measurement errors". Subsequently, a certain value is searched for, which is such a value that when the sample list is shifted by the certain value, the matching rate with "an m/z list that is assumed to be free of measurement errors" increases. This certain value corresponds to a measurement error. The certain value is searched for within the range of values a measurement error can assume.

The "m/z list that is assumed to be free of measurement errors" is, for example, an m/z list included in a specific m/z DB that is conceivable to be unlikely to include false peaks, but it is not limited to this example, and it may be, for example, an m/z list included in the total m/z DB, or may be another m/z list that is created for the purpose of measurement error correction of the sample list.

When correcting the m/z values in the sample list (when YES in ST34), in ST36, processor 10 estimates a measurement error included in the sample list, based on the specific m/z DB. In ST38, processor 10 performs correction, by shifting the m/z values in the sample list by a value of the measurement error thus estimated.

When not correcting the m/z values in the sample list (when NO in ST34) or after ST38, in ST40 to ST44, processor 10 compares the sample list with the m/z DB with weights assigned to m/z values for proteins included in the specific group, to identify the sample.

In ST40, processor 10 performs primary screening, namely, it selects, from the specific m/z DB, m/z lists of a certain rank or higher in terms of the rate of matching with the sample list. To be more specific, the "m/z lists of a certain rank or higher in terms of the rate of matching" refer to m/z lists, among the m/z lists in the m/z DB used for screening, that are of a certain rank or higher in terms of the rate of matching with the sample list. For example, top N1 m/z lists in terms of the matching rate are selected as the m/z lists of a certain rank or higher in terms of the rate of matching. N1 is an integer between 500 to 5000, for example. Another example of the "m/z lists of a certain rank or higher in terms of the rate of matching" are m/z lists that have a matching rate equal to or more than a certain value. The "m/z lists that have a matching rate equal to or more than a certain value" can be regarded as "m/z lists of a rank corresponding to the number of m/z lists that have a matching rate equal to or more than a certain value, or of a higher rank".

In ST42, processor 10 selects m/z lists, from the total m/z DB, that correspond to the top N1 m/z lists. In other words, it selects m/z lists, from the total m/z DB, for the genome that corresponds to the top N1 m/z lists.

In ST44, processor 10 performs secondary screening, namely, it selects, from among the m/z lists selected from the total m/z DB, m/z lists with high rates of matching with the sample list, to identify the sample. For example, top N2 m/z lists among the m/z lists selected from the total m/z DB are selected as the m/z lists with high matching rate. N1 is an integer that satisfies N2<N1, and, for example, it is an integer between 1 to 100.

After completing sample identification, in ST46, processor 10 reflects the taxonomic data in the identification results. For example, processor 10 adds microbial taxonomic information (such as family, genus, species, and phylogenetic group) corresponding to each of the N1 m/z lists thus selected.

Moreover, the N1 m/z lists may be organized based on the taxonomic data. For example, a table may be created in which the N1 m/z lists are sorted based on the taxonomic information. For example, a diagram may be created in which the microorganisms corresponding to the N1 m/z lists are arranged in the form of a phylogenetic tree. For example, the number of microorganisms, among those corresponding to the N1 m/z lists, that belong to a particular family, genus, species, or phylogenetic group may be expressed as numerical values. More specifically, a table may be created which describes the family, genus, species, or phylogenetic group to which the greatest number of microorganisms belong, among those corresponding to the N1 m/z lists. For example, the taxonomic data may be reflected in the N1 m/z lists to further narrow down the identification results. More specifically, a process may be applied such as removing an m/z list that is an obvious taxonomic outlier. By the above-described processes, it is possible to output identification results that reflect a taxonomic viewpoint. Moreover, the above-described processes may be performed based on two or more taxonomic systems. By this, it is possible to obtain identification results that reflect a plurality of taxonomic viewpoints.

In ST48, processor 10 determines whether to predict the proteins that correspond to the m/z values included in the sample list, namely, the proteins that are conceivable to be expressed in the sample. Whether or not to predict the proteins is set in advance by a user, for example.

When not predicting the proteins (when NO in ST48), in ST50, processor 10 outputs the identification results and ends the process. The outputting of the identification results is performed by displaying them on display 15, for example.

When predicting the proteins (when YES in ST48), in ST52, processor 10 links, to the m/z values included in the sample list, annotations about the corresponding proteins. As described above, the annotation is a piece of information regarding the protein, and it includes information regarding a group in which the protein is included. More specifically, for example, processor 10 adds, to the sample list, entries for the names and functions of the proteins corresponding to the m/z values. Moreover, for example, processor 10 may create a table, independently of the sample list, that includes the names and functions of the proteins corresponding to the m/z values included in the sample list.

After linking the protein annotations, in ST54, processor 10 outputs the identification results obtained in ST44, ST46 as well as the annotations associated in ST52 with the m/z values included in the sample list, and ends the process. The outputting of the identification results and the annotations is performed by displaying them on display 15, for example. In this way, with the information regarding the proteins whose expression is predicted from the sample list being output, the user can easily recognize the information regarding the proteins in the sample whose expression is predicted, and thereby can have a deeper understanding of the sample. Moreover, the information regarding the proteins can be referenced at the time of evaluating the sample identification results, and also can be referenced at the time of performing other analyses on the sample, leading to an enhanced user convenience.

The processes in FIG. 8 include both the primary screening based on the specific m/z DB and the secondary screening based on the total m/z DB, and this has the following advantages. Firstly, by performing the primary screening only on the m/z values of functionally-important and abundantly-expressed proteins, it is possible to select m/z lists with high matching rates under less influence of false peaks. Secondly, by performing the secondary screening on all the m/z values, it is possible to reflect the degree of similarity of other proteins, other than the proteins included in a specific group already screened by the primary screening.

The secondary screening may be performed only on the m/z values of proteins included in another specific group, which is a specific group different from the one in the primary screening. In this case, it is possible to perform sample identification, with attention paid to two types of important proteins.

Similarly, three or more different types of screening may be performed in combination.

In summary, apparatus 100 is capable of performing taxonomic sample identification by two or more screenings, which include a screening based on m/z values for proteins included in a specific group. In this way, by performing a plurality of different screenings, it is possible to take advantage of the characteristics of respective screenings to enhance the overall accuracy of sample identification.

Further, apparatus 100 can also be configured so that it can perform sample identification based on taxonomic data about microbial taxonomy.

For example, a specific m/z DB is constructed so that it includes only the m/z values for a group of proteins that are commonly expressed in a relatively high taxon (for example, a genus, which is taxonomically higher than species and strain). As a conceptual example, a case can be considered where the specific m/z DB includes a group (a group PA) of proteins that are commonly expressed in a genus A. In this case, by performing screening based on the specific m/z DB, it is possible to accurately determine whether the sample belongs to the genus A. Similarly, by constructing specific m/z DBs each of which includes a group of proteins that are commonly expressed in a certain genus, it is possible to screen based on the respective specific m/z DBs to accurately identify the genus of the sample. Then, it is possible to perform secondary screening to identify the species and/or strain within the genus thus identified. Hence, by the primary screening, it is possible to reduce the possibility of wrong determination of the genus of the sample, and, by the secondary screening, it is possible to screen in a manner suitable for identification of species and/or strain. As a result, it is possible to enhance the accuracy of sample identification.

(5-2. Assigning Weights by Scores)

In sample identification, the method for assigning weights to m/z values for proteins included in a specific group is not limited to the above-described method using a specific m/z DB. For example, another method may be adopted, in which, at the time of comparison between the sample list and the m/z lists included in the total m/z DB, the matching rate for a match with an m/z for a protein included in a specific group is calculated higher than for a match with an m/z for other proteins.

Figure 9:
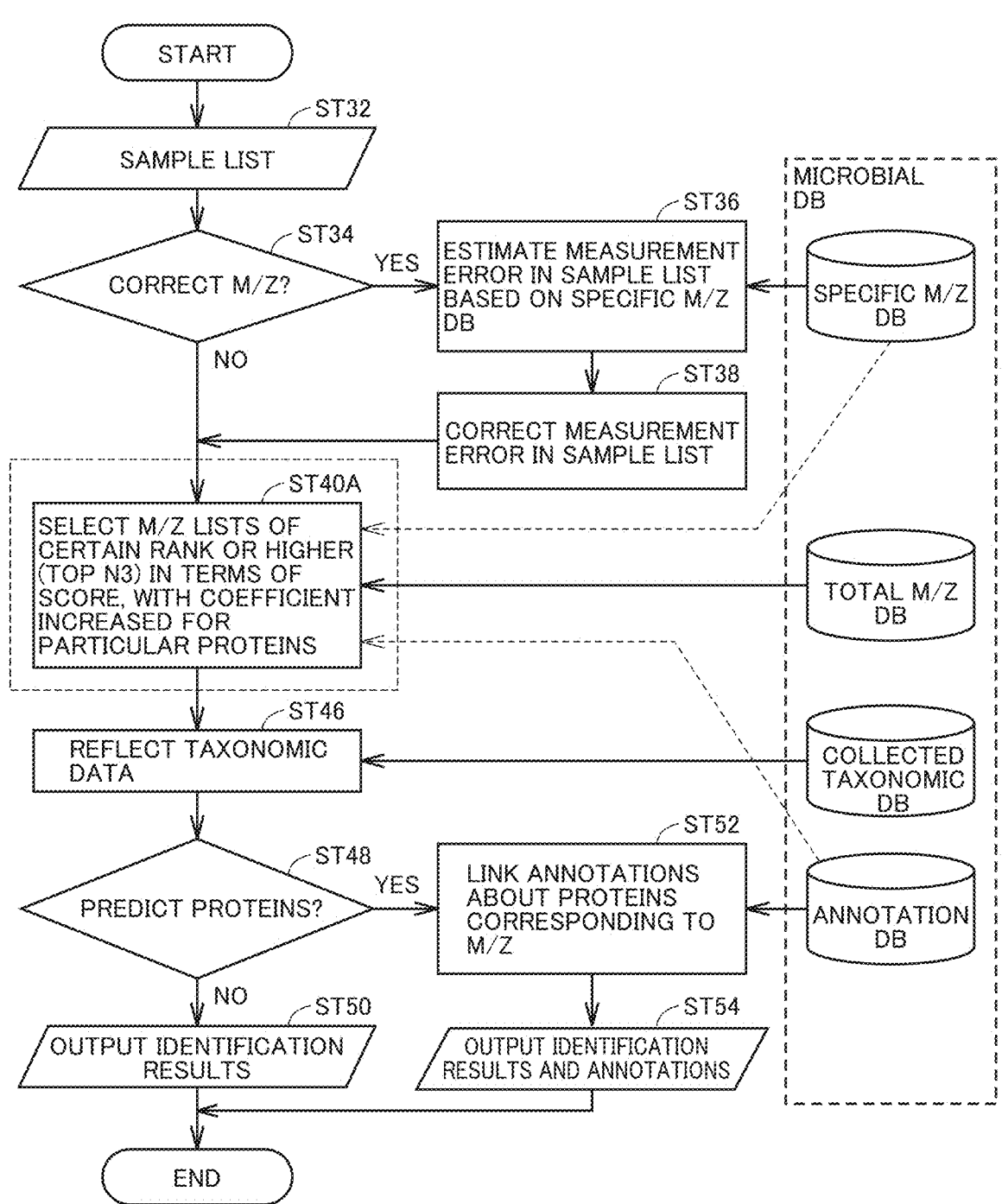
FIG. 9 is a flowchart illustrating another example of the processes related to identification of a sample.

FIG. 9 is a flowchart illustrating another example of the processes related to identification of a sample. The flowchart in FIG. 9 differs from the flowchart in FIG. 8 in that ST40 to ST42 are changed to ST40A, and the other steps in FIG. 9 are the same as in FIG. 8.

In ST40A in FIG. 9, processor 10 selects, from among the m/z lists in the total m/z DB, m/z lists with high rates of matching with the sample list. For example, from the total m/z DB, top N3 m/z lists are selected as the m/z lists with high matching rates. More specifically, firstly, as for each of the m/z lists included in the total m/z DB, processor 10 calculates a score by multiplying the number of matches between the m/z values included in the m/z list and the m/z values included in the sample list, by a certain coefficient. Then, from the total m/z DB, it selects m/z lists of a certain rank or higher in terms of the score. To be more specific, the "m/z lists of a certain rank or higher in terms of the score" are m/z lists of a certain rank or higher in terms of the score among the m/z lists in the m/z DB used for the screening. For example, top N3 m/z lists in terms of the score are selected as the m/z lists of a certain rank or higher in terms of the score. Another example of the "m/z lists of a certain rank or higher in terms of the score" are m/z lists that have a score equal to or more than a certain value. The "m/z lists that have a score equal to or more than a certain value" can be regarded as "m/z lists of a rank corresponding to the number of m/z lists that have a score equal to or more than a certain value, or of a higher rank".

The coefficient used at this time for calculating the score is defined to be greater for a match with an m/z for a protein included in a specific group, than for a match with an m/z not for a protein included in the specific group. For example, the coefficient is defined as 10. In other words, the score for a match with an m/z for a protein included in a specific group tends to be greater than for a match with an m/z for other proteins, and, as a result, the matching rate for the former case tends to be calculated higher. This allows for performing sample identification with weights assigned to the proteins included in the specific group. As a result, it is possible to perform sample identification with weights assigned to proteins that are unlikely to produce false peaks and that are functionally important and conserved, for example, and, thereby, the accuracy of sample identification is enhanced.

It should be noted that in ST40A, the m/z values for proteins included in the specific group may be selected because they are m/z values included in the specific m/z DB, but it may be selected by referencing to the annotation DB. Moreover, in the estimation of measurement errors in ST36 described above, it is not necessary to use the specific m/z DB. Hence, in a microbial identification method where assignment of weights is performed with the use of a coefficient for scores, it is not essential to construct a specific m/z DB.

Moreover, assignment of weights may be performed by a combination of a method that involves a plurality of screenings with the use of specific m/z DBs and a method that involves changing the coefficient for scores. For example, it is possible to perform, as the primary screening, screening with the use of a specific m/z DB of proteins in a certain group and, as the secondary screening, perform sample identification with a coefficient defined greater for a match with an m/z for a protein in other groups.

6. Experiment Examples

An example of an experiment performed with microbial identification system 1000 will be described.
(6-1. Construction of Database)

Genome sequences of bacteria and archaea were obtained from National Center for Biotechnology Information (NCBI) (U.S.) via the FTP server (with the use of RefSeq v95; at least 270,000 sequences). For all the genome sequences, gene estimation (with the use of Prodigal) was performed, and the loci and the products were predicted. Integrity of the results as well as contamination were estimated with checkM. Moreover, the number of contigs for each of the genome sequences, the number of undetermined bases (N), N50, and the number of genes for the genome base length were computed. N50 is an index of the quality of genomic information (assembly), and it is the weighted average of the sequence lengths of contigs in a genome sequence assembly. When adding up the lengths of the contigs in decreasing order of length until reaching half the total length, the resulting sequence length (base length) is N50. Each of the products (proteins) predicted from the estimated genes was subjected to methionine removal, prediction of signaling proteins, and prediction of the resulting cleaved fragments (with the use of SignalP), depending on the amino acid composition, and the mass of the final protein thus predicted was calculated. The resulting theoretical protein mass information was compiled into a database (a total m/z DB), and phylogenetic information (existing taxonomic information such as GTDB, Silva, and GreenGenes) was collected for each of the respective genomes and associated with one another with the use of the same ID to form a database (a taxonomic DB). In addition, for the respective gene products (proteins) thus predicted, with the use of the degree of similarity with the information registered in existing protein databases such as UniProKB and PFAM, the functions of the proteins were estimated and associated with the theoretical protein masses and protein names to form a database (an annotation DB).

Among all the genome sequences, any genome sequence that had any of the following reference values was regarded as a low-quality genome sequence and removed from the data: the estimated degree of integrity, 50% or less; contamination, 10% or more; the number of contigs, 1,000 or more; N50, 5 kbp or less; and the number of undetermined bases (N), 100,000 or more. In addition, any genome sequence that had (Number of genes)/(Total length of bases at loci in the genome) of 0.00180 or more was deleted.

Meanwhile, without consideration of these criteria, all the genome entries were compiled to construct a database and microbial identification was performed based on lists of measured protein peaks for known microbial strains acquired by MALDI-MS (AXIMA (registered trademark) manufactured by Shimadzu Corporation); as a result, the proportion of matches with genome entries having too many genes per genome was high, indicating that the results were not accurate.

The specific procedure of experiments on known microbial strains is described below. Microorganisms obtained from Biological Resource Center, National Institute of Technology and Evaluation (NBRC), and the like, such as bacteria and archaea including *Escherichia coli* NBRC 3301, *Bacillus subtilis* subsp. *subtilis* NBRC 13719, *Microlunatus phosphovorus* NBRC 101784, *Bifidobacterium longum* ATCC 15707, *Clostridium acetobutylicum* NBRC 13948, *Arthrobacter globiformis* NBRC 12137, *Brachybacterium conglomeratum* NBRC 15472, *Streptomyces griseus* subsp. *griseus* NBRC 12875, *Tetrasphaera duodecadis* NBRC 12959, *Bacteroides fragilis* ATCC 25285, *Sphingomonas yanoikuyae* NBRC 15102, *Xanthobacter autotrophicus* NBRC 102463, *Rhodobacter azotoformans* NBRC 16436, *Methanosarcina thermophila* MST-A1, and *Thauera linaloolentis* NBRC 102519, for example, were each incubated in a designated medium, and the culture medium was centrifuged (10000 g, 2 minutes) to remove the medium ingredients, followed by adding thereto the same amount of pure water to disperse bacterial cells and performing centrifugation under the same conditions to remove the supernatant. 500 µL of pure water was added to the resulting bacterial cell pellet to disperse the bacterial cells, and thereby a bacterial cell dispersion was obtained. To a 1.5-mL screwcap tube, 500 µL of zirconia beads (φ 0.5 mm) were added, and 500 µL of the above-mentioned bacterial cell dispersion was added. After the resultant was disrupted with a bead homogenizer (MS-100 manufactured by TOMY Seiko) at 4000 rpm for a total of 3 minutes and the liquid resulting from the disruption was centrifuged (15000 g, 5 minutes), 1 µL of the resulting supernatant was mixed with 9 µL of a 10-mg/ml CHCA (α-cyano-4-hydroxycinnamic acid) solution (50% aqueous acetonitrile solution containing 1% TFA (Trifluoroacetic Acid)), and 1 µL of the resultant was added dropwise to a MALDI-MS specimen plate, followed by air drying to prepare specimen/matrix-mixed crystals. The bacterial cell specimen was subjected to measurement in a MALDI-MS linear mode for the m/z range of 2000 to 20000, and thus MALDI mass spectra were obtained. Peak picking was performed to create a peak list that listed m/z values of the detected peaks as well as peak intensity (mV).

Subsequently, with the use of the database formed in the above manner, the degree of matching between the peaks in the peak list and the theoretical m/z values in the database was checked. As a result, many theoretical peaks estimated from the genomic information of the same bacterial species matched with the measured peaks within a certain proximity, but also included was genomic information that showed a high degree of matching with the theoretical peaks estimated from the genomic information of other bacterial species.

Figure 10:
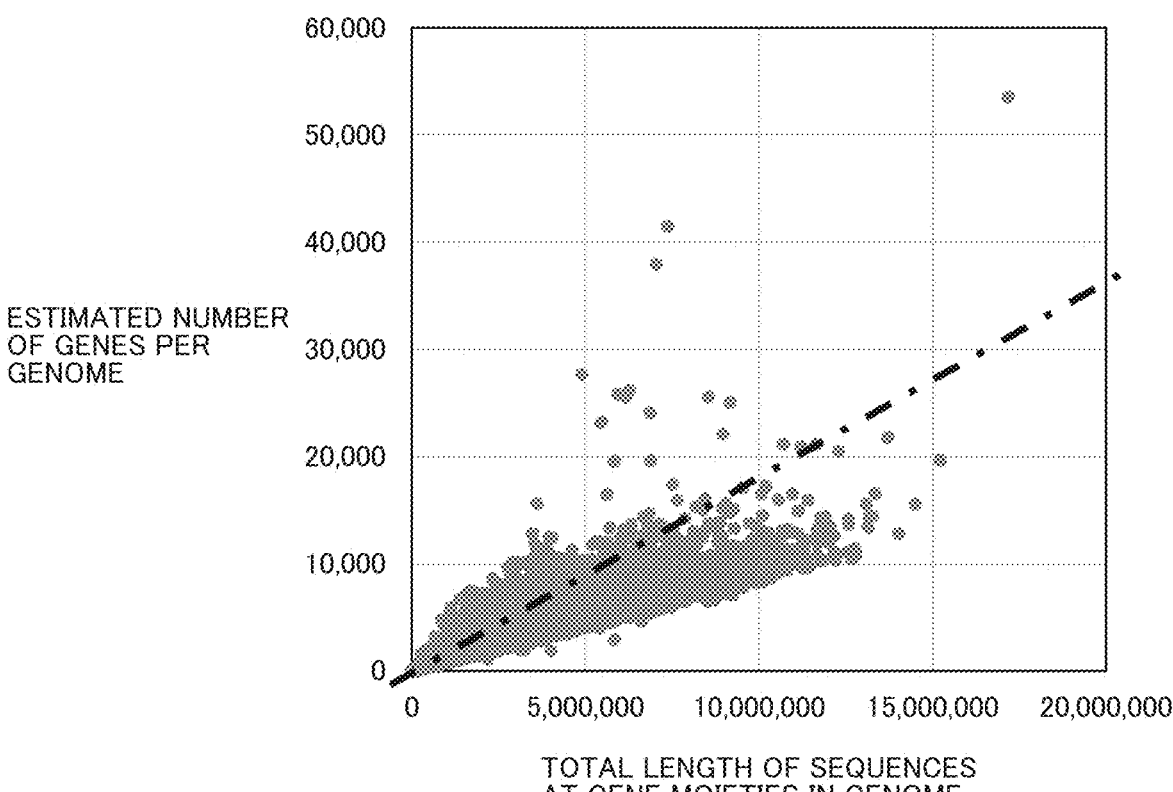
FIG. 10 is a view showing the relationship between the total number of base sequences at gene moieties in the genome and the estimated number of genes per genome.

FIG. 10 is a view showing the relationship between the total number of base sequences at gene moieties in the genome and the estimated number of genes per genome. More specifically, FIG. 10 shows the relationship between the base length at loci in the respective genomes estimated from the bacteria and archaea genomic information (at least 270,000 sequences) in RefSeq95, and the estimated number of genes. In FIG. 10, which shows the relationship between the total number of base sequences and the estimated genes for all the genome entries (at least 270,000 sequences), many genomes were detected above the dash-dot line in FIG. 10 (a line at which (Number of genes)/(Total length of bases at loci in the genome) is 0.00180). It was conjectured that due to, for example, errors in genome sequencing, proteins that are not actually present are also predicted and thereby the number of predicted theoretical peaks ends up being more than the actual number, consequently leading to false peak matches.

On the other hand, as a result of deleting, from the database, genome entries that have the (Number of genes)/

(Total length of bases at loci in the genome) data at about 0.00180 or higher, the degree of matching between the peak lists for the above-described microorganisms and the theoretical peaks estimated from the genomic information corresponding thereto increased. In other words, it was confirmed that deleting the genome entries detected above the dash-dot line in FIG. 10 from the database made it possible to perform proper evaluation. These results indicate that when constructing a database for microbial identification, it is essential to construct a database by properly sorting the genomic information registered in public databases in the above-described manner.

As a result of the above-described sorting, a total m/z DB consisting of 193,197 entries was formed. Meanwhile, another database consisting of species-level representatives from GTDB was formed, namely, a species-level representative database consisting of 31,760 entries.

(6-2. Construction of Algorithm)

Microorganisms obtained from NBRC and the like, such as bacteria and archaea including *Escherichia coli* NBRC 3301, *Bacillus subtilis* subsp. *subtilis* NBRC 13719, *Microlunatus phosphovorus* NBRC 101784, *Bifidobacterium longum* ATCC 15707, *Clostridium acetobutylicum* NBRC 13948, *Arthrobacter globiformis* NBRC 12137, *Brachybacterium conglomeratum* NBRC 15472, *Streptomyces griseus* subsp. *griseus* NBRC 12875, *Tetrasphaera duodecadis* NBRC 12959, *Bacteroides fragilis* ATCC 25285, *Sphingomonas yanoikuyae* NBRC 15102, *Xanthobacter autotrophicus* NBRC 102463, *Rhodobacter azotoformans* NBRC 16436, *Methanosarcina thermophila* MST-A1, and *Thauera linaloolentis* NBRC 102519, for example, were each incubated in a designated medium, and the culture medium was centrifuged (10000 g, 2 minutes) to remove the medium ingredients, followed by adding thereto the same amount of pure water to disperse bacterial cells and performing centrifugation under the same conditions to remove the supernatant. These microorganisms include a variety of phylogenetic groups such as aerobic and anaerobic bacteria and methanogenic archaea, with a variety of cell wall structures such as gram-positive and gram-negative ones, even including actinomycetes and the like. 500 µL of pure water was added to the resulting bacterial cell pellet to disperse the bacterial cells, and thereby a bacterial cell dispersion was obtained. To a 1.5-mL screwcap tube, 500 µL of zirconia beads (¢ 0.5 mm) were added, and 500 µL of the above-mentioned bacterial cell dispersion was added. After the resultant was disrupted with a bead homogenizer (MS-100 manufactured by TOMY Seiko) at 4000 rpm for a total of 3 minutes and the liquid resulting from the disruption was centrifuged (15000 g, 5 minutes), 1 µL of the resulting supernatant was mixed with 9 µL of a 10-mg/ml CHCA solution (50% aqueous acetonitrile solution containing 1% TFA) and 1 µL of the resultant was added dropwise to a MALDI-MS specimen plate, followed by air drying to prepare specimen/matrix-mixed crystals. Then, measurement was performed with MALDI-MS (AXIMA (registered trademark) manufactured by Shimadzu Corporation), and, thus, mass spectra for the test strains were obtained.

The theoretical peak list in the database formed in the above-described manner was compared with the measured peaks actually obtained from the incubated microorganisms. A measured peak and a theoretical peak were regarded as a peak match when they were detected within a certain proximity, and the number of peak matches was calculated for all the entries in the total m/z DB with the above-mentioned certain proximity being defined as 200 ppm; as a result, there were some cases where a genome entry with the highest degree of matching was not necessarily a genome entry corresponding to a test strain. Subsequently, a database consisting of proteins that are likely to be frequently detected in MALDI measurement was constructed (a specific m/z DB). Here, a two-step search algorithm was mounted, which was configured to operate as follows: extracting ribosomal proteins that are likely to be frequently detected, in reference to a database (an annotation DB); within the database thus constructed, selecting genome entries that have a high degree of matching with the measured peak lists (for example, extracting 500 to 5,000 entries); and, for the entries, calculating the degree of matching with the use of all the theoretical protein peak lists. As a result, an algorithm was constructed that was capable of selecting, from the measured peak lists, a genome entry closely related to each of all the 15 strains, and accurately estimating the phylogenetic taxon (genus, species), as shown in Table 1 below. Table 1 shows results of identification of bacteria and archaea that are in a wide range of phylogenetic groups and have a wide range of physiological characteristics and cell wall characteristics, by using the above-mentioned algorithm.

ratio lists, the mass-to-charge ratio lists being predicted for the respective sets of the genome data based on the proteins thus predicted.

With the method of constructing a microbial identification database according to Item 1, it is possible to construct a mass-to-charge ratio database based solely on the genome data in a genome database that satisfies a criterion. In other words, it is possible to enhance the quality of a mass-to-charge ratio database that is used in microbial identification based on mass spectrometry and that is constructed based on a genome database.

(Item 2) In the method of constructing a microbial identification database according to Item 1, the determining whether a criterion is satisfied may include determining based on whether a number of genes satisfies a reference value.

With the method of constructing a microbial identification database according to Item 2, a set of genome data wherein the number of genes estimated therefrom is outside a proper range is removed and not reflected in the mass-to-charge ratio database. As a result, the quality of the mass-to-charge ratio database is enhanced.

TABLE 1

| organism | strain | Top hit genome ID | Protein hit | Ribosomal protein hit | top_hit_oranism |
|---|---|---|---|---|---|
| Escherichia coli | NBRC 3301 | GCF_001894475.1 | 49 | 13 | Escherichia coli |
| Bacillus subtilis subsp. subtilis | NBRC 13719 | GCA_001698505.1 | 27 | 13 | Bacillus subtilis subsp. subtilis |
| Microlunatus phosphovorus | NBRC 101784 | GCF_000270245.1 | 26 | 17 | Microlunatus phosphovorus NM-1 |
| Bifidobacterium longum | ATCC 15707 | GCF_004334715.1 | 33 | 17 | Bifidobacterium longum subsp. longum |
| Clostridium acetobutylicum | NBRC 13948 | GCF_000008765.1 | 23 | 14 | Clostridium acetobutylicum ATCC 824 |
| Arthrobacter globiformis | NBRC 12137 | GCF_000238915.1 | 39 | 12 | Arthrobacter globiformis NBRC 12137 |
| Brachybacterium conglomeratum | NBRC 15472 | GCF_004362645.1 | 24 | 13 | Brachybacterium sp. AG952 |
| Streptomyces griseus subsp. griseus | NBRC 12875 | GCF_900105705.1 | 40 | 11 | Streptomyces griseus |
| Tetrasphaera duodecadis | NBRC12959 | GCF_002846495.1 | 22 | 13 | Tetrasphaera duodecadis |
| Bacteroides fragilis | ATCC 25285 | GCF_000025985.1 | 30 | 13 | Bacteroides fragilis NCTC 9343 |
| Sphingomonas yanoikuyae | NBRC 15102 | GCF_000315525.1 | 50 | 21 | Sphingobium yanoikuyae |
| Xanthobacter autotrophicus | NBRC 102463 | GCF_005871085.1 | 38 | 14 | Xanthobacter autotrophicus |
| Rhodobacter azotoformans | NBRC 16436 | GCF_003050905.1 | 33 | 15 | Rhodobacter azotoformans |
| Methanosarcina thermophila | MST-A1 | GCF_000969885.1 | 23 | 11 | Methanosarcina thermophila TM-1 |
| Thauera linaloolentis | NBRC 102519 | GCF_000310205.1 | 37 | 18 | Thauera linaloolentis 47Lol = DSM 12138 |

Aspects

As will be appreciated by those skilled in the art, the above-described example embodiments are specific examples of the below aspects.

(Item 1) A method of constructing a microbial identification database according to an aspect may comprise: acquiring genome data for microorganisms from a genome database; determining whether a criterion is satisfied by the genome data thus acquired; for respective sets of the genome data that were determined that they satisfied the criterion, predicting proteins to be expressed; and constructing a mass-to-charge ratio database including mass-to-charge (Item 3) In the method of constructing a microbial identification database according to Item 1 or Item 2, the determining whether a criterion is satisfied may include determining based on genome integrity.

With the method of constructing a microbial identification database according to Item 3, when the genome data is not of integrity, such as, for example, when a part of the genome data is lost or misread, the genome data is removed and not reflected in the mass-to-charge ratio database. As a result, the quality of the mass-to-charge ratio database is enhanced.

(Item 4) In the method of constructing a microbial identification database according to any one of Items 1 to 3, the determining whether a criterion is satisfied may include determining based on a genome contamination ratio.

With the method of constructing a microbial identification database according to Item 4, it is possible to remove genome data with a high contamination ratio. In other words, genome data in which DNA sequences of a plurality of types of microorganisms are highly likely mixed together is not reflected in the mass-to-charge ratio database. As a result, the quality of the mass-to-charge ratio database is enhanced.

(Item 5) In the method of constructing a microbial identification database according to any one of Items 1 to 4, the determining whether a criterion is satisfied may include determining based on a number of contigs.

With the method of constructing a microbial identification database according to Item 5, it is possible to remove genome data with a high number of contigs. When the number of contigs is too high, there is a possibility that a gene region to be expressed into a protein can be divided, potentially making it impossible to perform proper reading. Hence, by removing low-quality genome data based on the number of contigs, and thereby avoiding the genome data from being reflected in the mass-to-charge ratio database, it is possible to enhance the quality of the mass-to-charge ratio database.

(Item 6) In the method of constructing a microbial identification database according to any one of Items 1 to 5, the determining whether a criterion is satisfied may include determining based on a number of undetermined bases.

With the method of constructing a microbial identification database according to Item 6, it is possible to remove genome data with a high number of undetermined bases. From a DNA sequence that includes many undetermined bases, proper reading of the genes is highly likely impossible. Hence, by removing low-quality genome data based on the number of undetermined bases, and thereby avoiding the genome data from being reflected in the mass-to-charge ratio database, it is possible to enhance the quality of the mass-to-charge ratio database.

(Item 7) In the method of constructing a microbial identification database according to any one of Items 1 to 6, the constructing a mass-to-charge ratio database may include linking, to the proteins or mass-to-charge ratios thus predicted, information regarding a specific group in which the proteins thus predicted are included.

With the method of constructing a microbial identification database according to Item 7, it is possible to refer to the information regarding groups in which proteins are included, to selectively process mass-to-charge ratios for proteins included in a specific group. The specific group refers to "a group of proteins that are highly likely to be expressed in living microorganisms and highly likely to be detected as peaks at the time of mass spectrum measurement", for example.

(Item 8) In the method of constructing a microbial identification database according to Item 7, the information regarding a specific group may include at least one of protein name, protein function, and family.

With the method of constructing a microbial identification database according to Item 8, it is possible to selectively process mass-to-charge ratios for the same protein, or proteins having the same function, or proteins of the same family. For example, it is possible to perform sample identification with weights assigned to mass-to-charge ratios for "a group of proteins that are highly likely to be expressed in living microorganisms and highly likely to be detected as peaks at the time of mass spectrum measurement", based on the information about protein name, function, or family.

(Item 9) In the method of constructing a microbial identification database according to Item 7 or Item 8, the constructing a mass-to-charge ratio database may further include, based on the information regarding a specific group, constructing a specific mass-to-charge ratio database including specific mass-to-charge ratio lists only having mass-to-charge ratios predicted to be included in the specific group.

With the method of constructing a microbial identification database according to Item 9, use of the specific mass-to-charge ratio database makes it easier to selectively process mass-to-charge ratios for proteins included in the specific group. For example, it is made possible to perform screening based solely on mass-to-charge ratios for proteins included in the specific group.

(Item 10) In the method of constructing a microbial identification database according to any one of Items 7 to 9, the specific group may be selected based on at least one of the following criteria: a criterion that an expression amount is equal to or more than a certain threshold value; a criterion that a vital function is possessed; a criterion that at least a certain proportion of microorganisms share a degree of amino acid sequence similarity equal to or more than a certain threshold value; a criterion that each of the proteins is a basic protein; a criterion that a margin of error of mass-to-charge ratio analysis by MALDI-MS measurement is ±14 Da; a criterion that each of the proteins has a mass from 4 to 30 kDa; and a criterion that the specific group includes at least a certain number of types of proteins, and the vital function may include a function essential for at least one of cell maintenance and cell growth.

With the method of constructing a microbial identification database according to Item 10, it is possible to selectively process mass-to-charge ratios for "proteins that are highly likely to be expressed in a living thing and highly likely to be detected as peaks at the time of mass spectrum measurement" that satisfy the above-mentioned criteria.

(Item 11) In the method of constructing a microbial identification database according to any one of Items 7 to 10, the specific group may include at least one of ribosomal protein, chaperone, and DNA-binding protein.

With the method of constructing a microbial identification database according to Item 11, it is possible to selectively process mass-to-charge ratios for ribosomal proteins, chaperones, and DNA-binding proteins, which are "proteins that are highly likely to be expressed in a living thing and highly likely to be detected as peaks at the time of mass spectrum measurement". Hence, it is made possible to perform sample identification with weights assigned to such proteins.

(Item 12) In the method of constructing a microbial identification database according to any one of Items 1 to 6, the constructing a mass-to-charge ratio database may include constructing a total mass-to-charge ratio database including all predicted mass-to-charge ratios.

With the method of constructing a microbial identification database according to Item 12, use of the total mass-to-charge ratio database makes it possible to perform screening based on all mass-to-charge ratios. Hence, it is made possible to also reflect the degree of similarity of proteins other than the proteins included in the specific group, in sample identification.

(Item 13) In the method of constructing a microbial identification database according to any one of Items 7 to 11, the constructing a mass-to-charge ratio database may include constructing a total mass-to-charge ratio database including all predicted mass-to-charge ratios.

With the method of constructing a microbial identification database according to Item 13, use of the total mass-tocharge ratio database makes it possible to perform screening based on all mass-to-charge ratios. Hence, it is made possible to also reflect the degree of similarity of proteins other than the proteins included in the specific group, in sample identification.

(Item 14) The method of constructing a microbial identification database according to any one of Items 1 to 13 may further comprise acquiring taxonomic data about microbial taxonomy from a database that includes the taxonomic data. The constructing a mass-to-charge ratio database may include associating the taxonomic data with the mass-to-charge ratio database.

With the method of constructing a microbial identification database according to Item 14, it is made possible to associate genome IDs that are created based on the collected taxonomic data, with both the data included in the total mass-to-charge ratio database as well as the data included in the specific mass-to-charge ratio database. It is also possible to use the content of the collected taxonomic data for organizing the total mass-to-charge ratio database and the specific mass-to-charge ratio database, and/or to reflect the content of the former database in the content of the latter databases. In addition, it is also possible to use the collected taxonomic data for other purposes in the apparatus, such as for determining "particular proteins that are known to be noticeably expressed in a particular species".

(Item 15) In the method of constructing a microbial identification database according to any one of Items 1 to 14, the predicting may include: predicting genes from the genome data; predicting a post-translational amino acid sequence from the genes thus predicted; predicting post-translational modification from the post-translational amino acid sequence; and predicting a protein that includes the post-translational modification thus predicted.

With the method of constructing a microbial identification database according to Item 15, it is possible to predict, from genome data, proteins that can be expressed in the actual living body. This makes it possible to reflect the mass-to-charge ratios for proteins that are expressed in the actual living body, in the mass-to-charge ratio database, and thereby, the quality of a mass-to-charge ratio database is enhanced.

(Item 16) The method of constructing a microbial identification database according to any one of Items 1 to 15 may further comprise: adding new genome data to the mass-to-charge ratio database; determining whether a criterion is satisfied by the new genome data; when the criterion is satisfied by the new genome data, predicting proteins to be expressed from the new genome data, predicting mass-to-charge ratios based on results of the predicting, and predicting new mass-to-charge ratio lists; and adding the new mass-to-charge ratio lists to the mass-to-charge ratio database.

With the method of constructing a microbial identification database according to Item 16, it is possible to add the newly-acquired genome data to the m/z DB, and, thereby, it is possible to further enrich the content of the m/z DB. As a result, the quality of the m/z DB is further enhanced, and the accuracy of sample identification using the m/z DB is also further enhanced.

(Item 17) An apparatus configured to construct a microbial identification database according to an aspect constructs a microbial identification database by using genome data for microorganisms acquired from a genome database. The apparatus comprises a processor and a storage unit. The processor is configured to determine whether a criterion is satisfied by the genome data thus acquired. Moreover, the processor, for respective sets of the genome data that were determined that they satisfied the criterion, is configured to predict proteins to be expressed. Moreover, the processor is configured to construct a mass-to-charge ratio database including mass-to-charge ratio lists, the mass-to-charge ratio lists being predicted for the respective sets of the genome data based on the proteins thus predicted. Moreover, the processor is configured to store the mass-to-charge ratio database in the storage unit.

With the apparatus configured to construct a microbial identification database according to Item 17, it is possible to construct a mass-to-charge ratio database based solely on the genome data in a genome database that satisfies a criterion. In other words, it is possible to enhance the quality of a mass-to-charge ratio database that is used in microbial identification based on mass spectrometry and that is constructed based on a genome database.

It should be construed that embodiments disclosed herein are given by way of illustration in all respects, not by way of limitation. It is intended that the scope of the present invention is defined by claims, not by the above description, and encompasses all modifications and variations equivalent in meaning and scope to the claims.

REFERENCE SIGNS LIST 10 processor, 11 memory, 12 communication I/F, 13 input/output I/F, 14 operation unit, 15 display, 16 MS, 21 genome data collection unit, 22 genome data determination unit, 23 protein prediction unit, 24 construction unit, 25 storage unit, 31 acquisition unit, 32 sample identification unit, 33 annotation unit, 34 output unit, 70 public genome database, 80 public taxonomic database, 90 network, 100 apparatus, 101 controller, 321 primary screening unit, 322 secondary screening unit, 1000 microbial identification system.

The invention claimed is:

1. A method of constructing a microbial identification database, the method comprising:
   acquiring genome data for microorganisms from a genome database;
   determining whether a criterion is satisfied by the genome data thus acquired;
   for respective sets of the genome data that were determined that they satisfied the criterion, predicting proteins to be expressed; and
   constructing a mass-to-charge ratio database including mass-to-charge ratio lists, the mass-to-charge ratio lists being predicted for the respective sets of the genome data based on the proteins thus predicted.

2. The method of constructing a microbial identification database according to claim 1, wherein the determining whether a criterion is satisfied includes determining based on whether a number of genes satisfies a reference value.

3. The method of constructing a microbial identification database according to claim 1, wherein the determining whether a criterion is satisfied includes determining based on genome integrity.

4. The method of constructing a microbial identification database according to claim 1, wherein the determining whether a criterion is satisfied includes determining based on a genome contamination ratio.

5. The method of constructing a microbial identification database according to claim 1, wherein the determining whether a criterion is satisfied includes determining based on a number of contigs.

6. The method of constructing a microbial identification database according to claim 1, wherein the determining whether a criterion is satisfied includes determining based on a number of undetermined bases.

7. The method of constructing a microbial identification database according to claim 1, wherein the constructing a mass-to-charge ratio database includes linking, to the proteins or mass-to-charge ratios thus predicted, information regarding a specific group in which the proteins thus predicted are included.

8. The method of constructing a microbial identification database according to claim 7, wherein the information regarding a specific group includes at least one of protein name, protein function, and family.

9. The method of constructing a microbial identification database according to claim 7, wherein the constructing a mass-to-charge ratio database further includes, based on the information regarding a specific group, constructing a specific mass-to-charge ratio database including specific mass-to-charge ratio lists only having mass-to-charge ratios predicted to be included in the specific group.

10. The method of constructing a microbial identification database according to claim 7, wherein the specific group is selected based on at least one of the following criteria: a criterion that an expression amount is equal to or more than a certain threshold value; a criterion that a vital function is possessed; a criterion that at least a certain proportion of microorganisms share a degree of amino acid sequence similarity equal to or more than a certain threshold value; a criterion that each of the proteins is a basic protein; a criterion that a margin of error of mass-to-charge ratio analysis by MALDI-MS measurement is +14 Da; a criterion that each of the proteins has a mass from 4 to 30 kDa; and a criterion that the specific group includes at least a certain number of types of proteins, and the vital function includes a function essential for at least one of cell maintenance and cell growth.

11. The method of constructing a microbial identification database according to claim 7, wherein the specific group includes at least one of ribosomal protein, chaperone, and DNA-binding protein.

12. The method of constructing a microbial identification database according to claim 1, wherein the constructing a mass-to-charge ratio database includes constructing a total mass-to-charge ratio database including all predicted mass-to-charge ratios.

13. The method of constructing a microbial identification database according to claim 7, wherein the constructing a mass-to-charge ratio database further includes constructing a total mass-to-charge ratio database including all predicted mass-to-charge ratios.

14. The method of constructing a microbial identification database according to claim 1, further comprising acquiring taxonomic data about microbial taxonomy from a database that includes the taxonomic data, wherein the constructing a mass-to-charge ratio database includes associating the taxonomic data with the mass-to-charge ratio database.

15. The method of constructing a microbial identification database according to claim 1, wherein the predicting includes:

predicting genes from the genome data;

predicting a post-translational amino acid sequence from the genes thus predicted;

predicting post-translational modification from the post-translational amino acid sequence; and predicting a protein that includes the post-translational modification thus predicted.

16. The method of constructing a microbial identification database according to claim 1, further comprising:

adding new genome data to the mass-to-charge ratio database;

determining whether a criterion is satisfied by the new genome data;

when the criterion is satisfied by the new genome data, predicting proteins to be expressed from the new genome data, predicting mass-to-charge ratios based on results of the predicting, and predicting new mass-to-charge ratio lists; and adding the new mass-to-charge ratio lists to the mass-to-charge ratio database.

17. An apparatus configured to construct a microbial identification database by using genome data for microorganisms acquired from a genome database, the apparatus comprising:

a processor; and a storage unit, wherein the processor is configured to determine whether a criterion is satisfied by the genome data thus acquired, for respective sets of the genome data that were determined that they satisfied the criterion, predict proteins to be expressed, construct a mass-to-charge ratio database including mass-to-charge ratio lists, the mass-to-charge ratio lists being predicted for the respective sets of the genome data based on the proteins thus predicted, and store the mass-to-charge ratio database in the storage unit.

* * * * *